(12) United States Patent
Corl et al.

(10) Patent No.: US 7,630,747 B2
(45) Date of Patent: Dec. 8, 2009

(54) APPARATUS FOR ASCERTAINING BLOOD CHARACTERISTICS AND PROBE FOR USE THEREWITH

(75) Inventors: Paul D. Corl, Palo Alto, CA (US); Harry D. Nguyen, Garden Grove, CA (US); Amos Gottlieb, San Francisco, CA (US); Margaret R. Webber, Los Altos, CA (US)

(73) Assignee: Keimar, Inc., Pleasanton, CA (US)

( * ) Notice: Subject to any disclaimer, the term of this patent is extended or adjusted under 35 U.S.C. 154(b) by 470 days.

(21) Appl. No.: 10/658,926

(22) Filed: Sep. 9, 2003

(65) Prior Publication Data

US 2005/0054905 A1 Mar. 10, 2005

(51) Int. Cl.
*A61B 5/05* (2006.01)
(52) U.S. Cl. .............. 600/345; 600/364; 600/348; 600/353; 600/355; 600/361
(58) Field of Classification Search ............... 600/345, 600/347, 348, 365, 372, 331–332, 381, 434, 600/322–327, 364
See application file for complete search history.

(56) References Cited

U.S. PATENT DOCUMENTS

| | | | |
|---|---|---|---|
| 2,562,544 A | 7/1951 | Gleason | |
| 3,434,869 A | 3/1969 | Davidson | |
| 3,518,982 A | 7/1970 | Timmins et al. | |
| 3,865,897 A | 2/1975 | Falender et al. | |
| 3,893,448 A * | 7/1975 | Brantigan | 600/364 |
| 3,905,888 A | 9/1975 | Mindt et al. | |
| 3,938,502 A | 2/1976 | Bom | |
| 4,015,600 A | 4/1977 | Liautaud | |
| 4,016,864 A * | 4/1977 | Sielaff et al. | 600/364 |
| 4,068,659 A * | 1/1978 | Moorehead | 604/508 |

(Continued)

FOREIGN PATENT DOCUMENTS

EP 0083969 A 7/1983

(Continued)

OTHER PUBLICATIONS

Kazuhiko Ishihara et al., "*Photoinduced graft polymerization of 2-methacryloyloxyethyl phosphorylcholine on polyethylene membrane surface for obtaining blood cell adhesion resistance*", republished in Elsevier Science B.V., PII: S0927-7765(99)00158-7, Colloids and Surfaces B: Biointerfaces 18 (2000) pp. 325-335.

(Continued)

*Primary Examiner*—Patricia C Mallari
*Assistant Examiner*—Karen E Toth
(74) *Attorney, Agent, or Firm*—Knobbe, Martens, Olson & Bear, LLP

(57) ABSTRACT

An apparatus for use with a patient having a vessel carrying blood to ascertain characteristics of the blood. The apparatus includes a display module and a probe having a distal extremity adapted to be inserted into the vessel of the patient and having a proximal extremity coupled to the display module. The probe includes a sensor in the distal extremity for providing an electrical signal to the display module when the probe is disposed in the blood. The probe can have an antithrombogenic surface treatment for inhibiting the adhesion of blood components to the probe when disposed in the blood.

9 Claims, 14 Drawing Sheets

U.S. PATENT DOCUMENTS

| | | | |
|---|---|---|---|
| 4,166,469 A * | 9/1979 | Littleford | 607/122 |
| 4,221,567 A | 9/1980 | Clark et al. | |
| 4,364,625 A | 12/1982 | Baker et al. | |
| 4,474,183 A * | 10/1984 | Yano et al. | 600/353 |
| 4,573,481 A * | 3/1986 | Bullara | 607/118 |
| 4,673,584 A | 6/1987 | Nygren et al. | |
| 4,819,655 A | 4/1989 | Webler | |
| 4,832,034 A * | 5/1989 | Pizziconi et al. | 600/366 |
| 4,861,454 A * | 8/1989 | Ushizawa et al. | 204/414 |
| 4,874,500 A | 10/1989 | Madou et al. | |
| 4,919,141 A | 4/1990 | Zier et al. | |
| 5,007,424 A | 4/1991 | Ahsbahs | |
| 5,054,882 A * | 10/1991 | Riccitelli et al. | 385/12 |
| 5,070,882 A | 12/1991 | Bui et al. | |
| 5,165,407 A * | 11/1992 | Wilson et al. | 600/345 |
| 5,240,004 A | 8/1993 | Walinsky et al. | |
| 5,322,063 A | 6/1994 | Allen et al. | |
| 5,333,609 A * | 8/1994 | Bedingham et al. | 600/339 |
| 5,391,250 A * | 2/1995 | Cheney et al. | 156/268 |
| 5,409,666 A | 4/1995 | Nagel et al. | |
| 5,497,772 A * | 3/1996 | Schulman et al. | 600/347 |
| 5,596,988 A * | 1/1997 | Markle et al. | 600/353 |
| 5,651,767 A | 7/1997 | Schulman et al. | |
| 5,655,529 A * | 8/1997 | Pontzer | 600/365 |
| 5,662,960 A | 9/1997 | Hostettler et al. | |
| 5,788,647 A | 8/1998 | Eggers | |
| 5,928,155 A | 7/1999 | Eggers et al. | |
| 5,944,695 A | 8/1999 | Johnson et al. | |
| 5,971,934 A | 10/1999 | Scherer et al. | |
| 5,997,517 A | 12/1999 | Whitbourne | |
| 6,064,900 A | 5/2000 | Vadgama et al. | |
| 6,248,067 B1 | 6/2001 | Causey et al. | |
| 6,254,586 B1 | 7/2001 | Mann et al. | |
| 6,306,103 B1 * | 10/2001 | Tyler | 600/573 |
| 6,503,225 B1 * | 1/2003 | Kirsch et al. | 604/126 |
| 6,607,477 B1 * | 8/2003 | Longton et al. | 600/3 |
| 6,616,614 B2 | 9/2003 | Webber et al. | |
| 6,965,791 B1 * | 11/2005 | Hitchcock et al. | 600/345 |
| 7,491,175 B2 | 2/2009 | Ruether et al. | |
| 2001/0029337 A1 * | 10/2001 | Pantages et al. | 600/463 |
| 2001/0051768 A1 * | 12/2001 | Schulman et al. | 600/345 |
| 2002/0052563 A1 | 5/2002 | Penn et al. | |
| 2003/0009095 A1 | 1/2003 | Skarda | |
| 2003/0050547 A1 * | 3/2003 | Lebel et al. | 600/364 |
| 2003/0055353 A1 * | 3/2003 | Webber et al. | 600/526 |
| 2003/0078481 A1 | 4/2003 | McIvor et al. | |
| 2003/0105453 A1 | 6/2003 | Stewart | |
| 2004/0111141 A1 * | 6/2004 | Brabec et al. | 607/119 |
| 2004/0162472 A1 | 8/2004 | Berson et al. | |
| 2005/0272989 A1 | 12/2005 | Shah et al. | |
| 2006/0229511 A1 | 10/2006 | Fein et al. | |
| 2006/0235314 A1 * | 10/2006 | Migliuolo et al. | 600/505 |
| 2006/0243061 A1 | 11/2006 | Krivitski et al. | |
| 2008/0125632 A1 | 5/2008 | Corl et al. | |
| 2008/0125633 A1 | 5/2008 | Corl et al. | |
| 2008/0125635 A1 | 5/2008 | Corl et al. | |
| 2008/0139909 A1 | 6/2008 | Corl et al. | |
| 2008/0146903 A1 | 6/2008 | Corl et al. | |

FOREIGN PATENT DOCUMENTS

| | | |
|---|---|---|
| EP | 0891807 A | 1/1999 |
| WO | WO 9510975 A | 4/1995 |

OTHER PUBLICATIONS

Written Opinion of the International Searching Authority, Application No. PCTUS0429558, Apr. 10, 2007.

European Patent Office, Supplementary European Search Report, Application No. EP04783696, Dec. 4, 2007.

Patent Office of the People's Republic of China, First Office Action, Application No. 200480030397.3, May 9, 2008.

Examination Report for European Application No. 04783696.0, dated May 29, 2008.

International Search Report for PCT Application No. PCT/US03/08043, dated Nov. 28, 2003.

Office Action for U.S. Appl. No. 09/956,064, dated Oct. 29, 2002.

Office Action for U.S. Appl. No. 12/027,898, dated Mar. 26, 2009.

Restriction Requirement for U.S. Appl. No. 12/027,902, dated Apr. 30, 2009.

Office Action for U.S. Appl. No. 12/027,905, dated Mar. 30, 2009.

International Search Report for PCT Application No. PCT/US2004/29558, dated Apr. 10, 2007.

Ganter et al., "Continuous intravascular blood gas monitoring: development, current techniques, and clinical use of a commercial device" *British Journal of Anaesthesia* 91(3): 397-407 (2003).

Notice of Allowance for U.S. Appl. No. 09/956,065, dated Apr. 7, 2003.

* cited by examiner

Chart 1: Oxygen sensor performance

Chart 2: Oxygen sensor response

Chart 3: Oxygen sensor longevity

Chart 4: Carbon dioxide sensor performance

Chart 5. Carbon dioxide sensor response

Chart 6: pH sensor performance

APPARATUS FOR ASCERTAINING BLOOD CHARACTERISTICS AND PROBE FOR USE THEREWITH

TECHNICAL FIELD

This invention relates to an apparatus for measuring physiological parameters in an individual and, in particular, to an apparatus and method for measurement of blood gas parameters of a patient.

BACKGROUND OF THE INVENTION

Determination of cardiac output, arterial blood gases, and other hemodynamic or cardiovascular parameters is critically important in the treatment and care of patients, particularly those undergoing surgery or other complicated medical procedures and those under intensive care. Typically, cardiac output measurements have been made using pulmonary artery thermodilution catheters, which can have inaccuracies of 20% or greater. It has been found that the use of such thermodilution catheters increases hospital costs while exposing the patient to potential infectious, arrhythmogenic, mechanical, and therapeutic misadventure. Blood gas measurements have also heretofore been made. Commonly used blood gas measurement techniques require a blood sample to be removed from the patient and transported to a lab analyzer for analysis. The caregiver must then wait for the results to be reported by the lab, a delay of 20 minutes being typical and longer waits not unusual.

More recent advances in the art have provided for "point-of-care" blood testing systems wherein testing of blood samples is performed at a patient's bedside or in the area where the patient is located. Such systems include portable and handheld units and modular units which fit into a bedside monitor. While most point-of-care systems require the removal of blood from the patient for bedside analysis, a few do not. In such systems, intermittent blood gas measurements are made by drawing a sufficiently large blood sample into an arterial line to ensure an undiluted sample at a sensor located in the line. After analysis, the blood is returned to the patient, the line is flushed, and results appear on the bedside monitor.

A non-invasive technology, pulse oximetry, is available for estimating the percentage of hemoglobin in arterial blood that is saturated with oxygen. Although pulse oximeters are capable of estimating arterial blood oxygen content, they are not capable of measuring carbon dioxide, pH, or venous oxygen content. Furthermore, ex vivo pulse oximetry is commonly performed at the fingertip and can be skewed by peripheral vasoconstriction or even nail polish.

Unfortunately, none of the available systems or methods for blood gas analysis provide for accurate, direct and continuous in vivo measurements of arterial and venous oxygen partial pressures, carbon-dioxide partial pressure, pH, and cardiac output, while presenting minimal risk to the patient.

Coatings and their applications to medical devices have heretofore been described. See, for example, U.S. Pat. Nos. 3,443,869, 4,673,584, 5,997,517 and 5,662,960. Coatings have been employed to maintain lubricity while minimizing complications arising from use of exogenous material in vivo. Certain coatings require reapplication to maintain lubricity and certain lubricious coatings require administration of heparinized saline to maximize immunological tolerance. For devices such as catheters and probes, extraction from a physiological environment for reapplication of a lubricant increases operational costs as well as exposing the patient to heightened risk of mechanical and therapeutic misadventure. Furthermore, reapplication of a coating can compromise the gas permeability of the membrane upon which the coating is applied.

SUMMARY OF THE INVENTION

An apparatus for use with a patient having a vessel carrying blood to ascertain characteristics of the blood is provided. The apparatus includes a display module and a probe having a distal extremity adapted to be inserted into the vessel of the patient and having a proximal extremity coupled to the display module. The probe includes a sensor in the distal extremity for providing an electrical signal to the display module when the probe is disposed in the blood. The probe can have an antithrombogenic surface treatment for inhibiting the adhesion of blood components to the probe when disposed in the blood.

BRIEF DESCRIPTION OF THE DRAWINGS

For a better understanding of the nature and details of the invention, reference should be made to the following drawings, which in some instances are schematic in detail and wherein like reference numerals have been used throughout.

Like reference numerals refer to corresponding parts throughout the several views of the drawings.

DETAILED DESCRIPTION OF THE PREFERRED EMBODIMENTS

Figure 1:
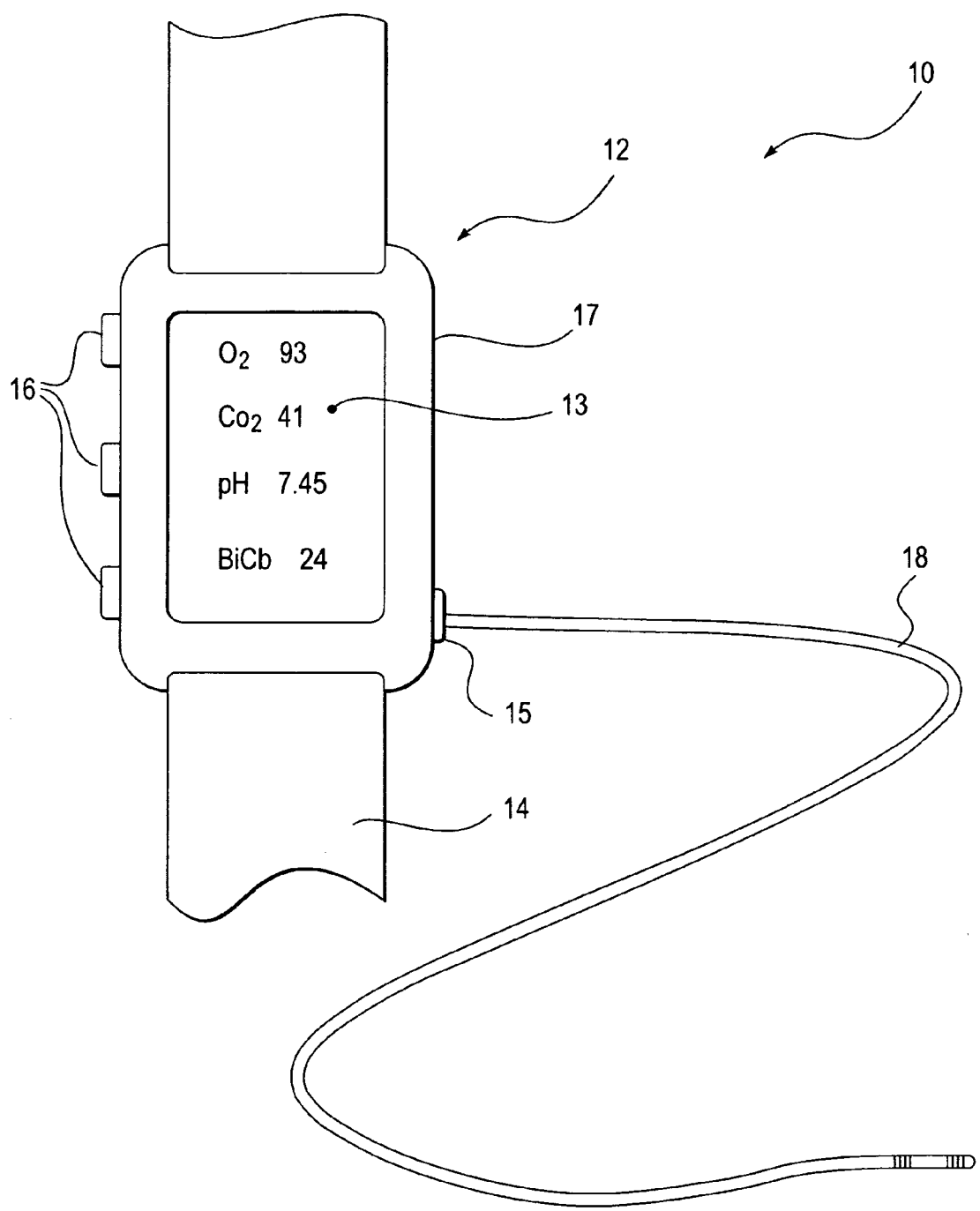
FIG. 1 is an isometric view of an example of an apparatus according to the present invention having a display module and a probe for monitoring physiological parameters.

Referring to FIG. 1, an apparatus 10 according to the present invention for making intravascular measurement of physiological parameters or characteristics generally includes a display module 12 and one or more probes 18. As described in more detail herein, the display module 12 and probe 18 are particularly adapted for accurate and continuous in vivo measurement and display of intravascular parameters such as partial pressure of oxygen ($PO_2$), partial pressure of carbon dioxide ($PCO_2$), and pH. In addition, cardiac output (CO) can be calculated by combining two measurements of $PO_2$ obtained from a pair of probes, one disposed in an artery and the other in a vein. Alternatively, or in addition to the aforementioned sensors, the probe 18 may include sensors for other useful blood parameters such as potassium, sodium, bilirubin, hemoglobin, glucose, pressure, etc. Additional features of the display module 12 and probe 18 are detailed hereinafter and in copending U.S. patent application Ser. No. 09/956,064 filed Sep. 18, 2001 and now U.S. Pat. No. 6,616,614, the entire content of which is incorporated herein by this reference.

Figure 2:
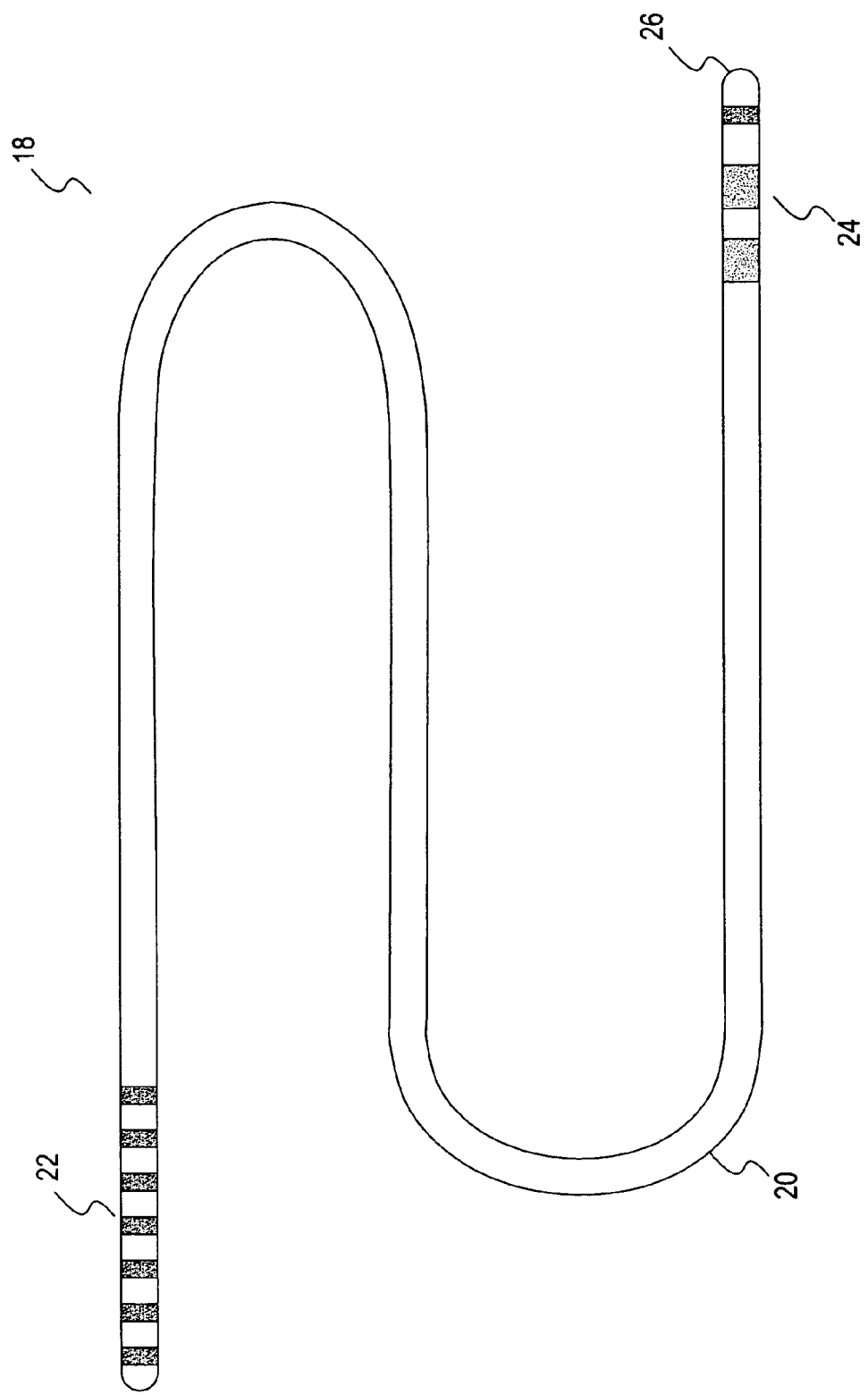
FIG. 2 is an isometric view of the probe of FIG. 1.

As described herein, probe 18 removably connects to and communicates with display module 12 by way of first or module connector 15 and mating second or probe connector 22 located at the proximal end or extremity of probe 18. Preferably, as shown in FIG. 2, probe 18 comprises a flexible elongate probe body or cannula 20 formed of a polymer or other suitable insulating material, having a substantially uniform diameter over its entire length. The probe body 20 supports a number of electrical contacts, and preferably at least two, comprising a low-profile electrical connector 22, and it includes a sensor section 24 and a blunt tip 26 near the distal end or extremity of the probe 18. Electrical conductors attached to the electrodes in the sensor section 24 of the probe 18 pass through the length of the cannula 20, preferably through a bore or lumen provided in the tubular cannula, and attach to the connector 22. The sensor section 24 of the probe 18 includes electrodes inside an electrolyte-filled chamber. A gas permeable window preferably covers at least a portion of the chamber. All of the probe elements are dimensioned to fit substantially within the diameter of the probe body 20, having a diameter in the range from 0.010" to 0.035", but preferably a diameter of 0.020", such that the entire probe 18, including the low-profile connector 22, may be passed through the inner bore of a suitable introducer, such as a hypodermic needle, of a size suitable for accessing a blood vessel in the hand, wrist, or forearm. Depending on the diameter of the probe body 20, a suitable hypodermic needle for this purpose could be as small as 25-gauge having an inner diameter of at least 0.010 inch, and it could be as large as 18-gauge having an inner diameter of at least 0.035 inch, with the preferred size of 20-gauge having an inner diameter of at least 0.023 inch, suitable for use with a probe body having a nominal diameter of 0.020 inch. In this preferred embodiment, the probe 18 can have a suitable length such as 25 centimeters, permitting the sensor section 24 near the distal end of the probe 18 to be inserted into a blood vessel in the hand, wrist, or forearm, while the low-profile connector 22 at the proximal end or extremity of probe 18 is connected to the display module 12, which can be strapped to the wrist of the patient.

The low profile connector 22 is advantageous in this application, since it permits the use of an ordinary hypodermic needle or other suitable introducer to introduce the probe 18 into the blood vessel with minimal trauma to the wall of the blood vessel. The probe 18 is introduced into the blood vessel by first inserting the appropriately sized hypodermic needle through the skin and into the target vessel. The extremely sharp tip of the hypodermic needle easily penetrates the skin, the underlying tissue, and the vessel wall, while producing minimal trauma. Once the hypodermic introducer needle has entered the target blood vessel, the probe 18 is inserted through the bore of the needle and advanced into the vessel. The blunt tip 26 and the lubricious surface treatment 38 on the probe 18 minimize the likelihood of vessel trauma as the probe 18 is advanced within the target vessel. Once the probe 18 is properly positioned within the target vessel, the introducer needle is withdrawn from the artery and the skin, and completely removed from the probe 18 by sliding it off the proximal end of the probe 18 over the low profile connector 22, leaving the probe 18 in place in the vessel. The small puncture left by the hypodermic needle quickly seals around the body of the probe 18, thereby preventing excessive bleeding. The puncture site is covered with a bandage and tape to guard against infection and to anchor the probe. Any blood residue on the low profile connector 22 or the exposed portion of the probe 18 is wiped away with a moist pad or alcohol swab, and the probe connector 22 is then attached to the mating connector 15 on the display module 12. In contrast to the simple, minimally traumatic introduction method facilitated by the low-profile connector, a conventional probe, having a standard connector, requires the use of a split introducer sheath to introduce the probe into the blood vessel. The split introducer sheath, which is blunter and bulkier than a hypodermic needle, is much more likely to stretch or tear the vessel wall, thereby increasing the risk of complications such as bleeding or prolonged healing time. Although probe 18 has been described for use in a blood vessel, it should be appreciated that the probe can be introduced into other vessels, lumen or tissue of a body of a patient, by means of any suitable introducer, and be within the scope of the present invention.

Figure 3:
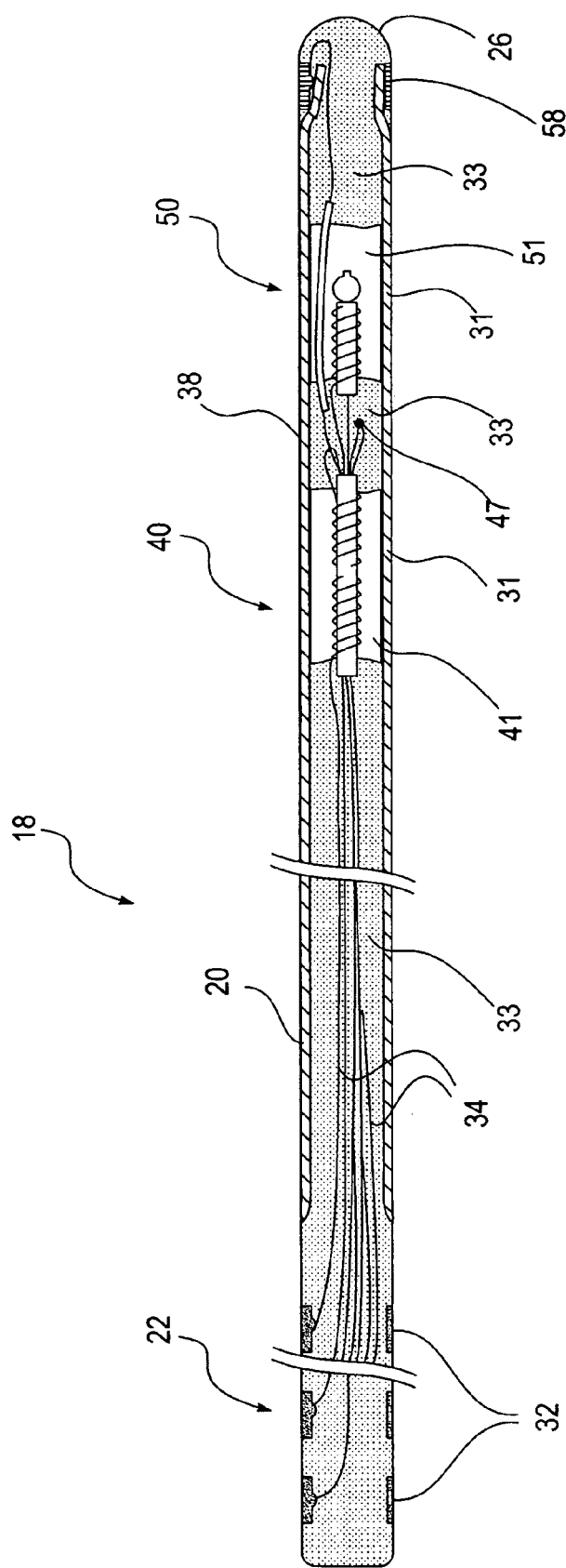
FIG. 3 is an enlarged cross-sectional view of the probe of FIG. 1 adapted for multi-parameter measurement.

In a preferred embodiment, illustrated in FIG. 3, the probe 18 is formed from a cannula, sleeve or body 20 of a suitable polymer material, which serves the purpose of constituting a structural element of the probe 18. All or a portion of the body 20 can also serve as a gas permeable membrane enclosing or surrounding at least the sensor chambers 41 and 51. The polymer sleeve material provides strength and flexibility to serve as a structural element of the probe 18. It also permits the passage of oxygen and carbon dioxide gases while blocking the passage of liquid water and the ions dissolved therein when serving as the gas permeable membrane. The sleeve 20 defines the outer surface of a major portion of the probe 18, and the substantial majority of the sleeve 20 is preferably filled with a flexible polymer 33 such as ultraviolet-cured adhesive to provide robustness to the probe body 20, to anchor the electrical conductors 34 and sensor electrode assemblies, and to seal the ends of the sensor chambers 41 and 51. The sleeve 20 provides a substantial portion of the probe strength, particularly in the sensor segment 24, where the sensor chambers 41 and 51 are filled with liquid, and the sleeve 20 can also form the circumferential windows 31 enclosing said sensor chambers when all or a portion of the sleeve is made from a gas permeable material.

A preferred material for the sleeve 20 shown in FIG. 3 is plastic, preferably a polymer and more preferably polymethylpentene. The sleeve 20 has a wall thickness in the range from 0.001 inch to 0.003 inch and preferably 0.0015 inch. Among commonly-used polymers suitable for extrusion as thin-walled tubing, polymethylpentene has among the highest oxygen and carbon dioxide permeability coefficients available. In addition, it has great stiffness. Table 1 includes gas permeability coefficients and the stiffness-related modulus of elasticity of a representative selection of commonly-used polymer materials, showing the advantages of polymethylpentene for this application.

| Material | $CO_2$ permeability (Barrer[1]) | $O_2$ permeability (Barrer[1]) | Tensile Modulus (GPa) |
| --- | --- | --- | --- |
| Polymethylpentene | 80 | 27 | 1.5 |
| Low Density Polyethylene | 13 | 10 | 0.1-0.3 |
| Polytetrafluoroethylene | 10 | 4.3 | 0.3-0.8 |
| Polypropylene | 8 | 2.3 | 0.9-1.5 |
| Polycarbonate | 6.4 | 1.4 | 2.3-2.4 |
| Polyimide | 0.3 | 0.15 | 2-3 |
| Polyester | 0.13 | 0.05 | 2-4 |
| Nylon | 0.09 | 0.04 | 2.6-3.0 |

[1]The Barrer is a unit of gas permeability, equivalent to $10^{-10}$ ($cm^3$ per second of gas at standard temperature and pressure) (cm of membrane thickness) per ($cm^2$ of membrane area) per (cmHg of pressure)

A cylindrical sleeve 20 of gas permeable membrane material is particularly advantageous as the covering for the blood gas sensor chamber 41 or 51, since it creates a complete circumferential window 31, thereby maximizing the membrane area for a given sensor length. In addition to maximizing the membrane area, the circumferential window 31 inhibits the "wall effect" artifact seen in previous blood gas sensor probes, wherein the gas permeable membrane on the tip or one side of a blood gas sensor probe is fully or partially blocked from exposure to the blood when the probe is inadvertently positioned against a vessel wall. The circumferential window of the present invention precludes the possibility for a substantial portion of the membrane to be blocked by close proximity of the probe to the wall of the blood vessel. For the carbon dioxide sensor, the flow of gas through the membrane mainly affects the response time of the sensor. The electrolyte or other solution inside the carbon dioxide sensor chamber eventually reaches carbon dioxide equilibrium with the surrounding blood, as long as there is a reasonable rate of diffusion through the membrane. However, the oxygen sensor relies on a continuous flow of oxygen through the membrane to be consumed at the platinum sensing electrode, therefore, any significant obstruction to the flow of oxygen to the sensing electrode can affect the accuracy of the sensor. The sensitivity of the oxygen sensor to the "wall effect" is minimized by making the membrane permeability so high that the reaction rate is limited primarily by the rate of consumption of oxygen at the sensing electrode, which is then determined by the exposed area of platinum catalyst. In this case, any effect on the probe due to a partial blockage of the circumferential window 31 by close proximity to the wall of a blood vessel is minimized.

The probe body 20 supports electrical contacts 32 constituting the low-profile electrical connector 22 and it contains the electrical conductors 34 and the sensor section 24 of the probe 18. The electrical contacts 32 consist of gold bands or the like, soldered or welded to the electrical conductors 34, which are electrically coupled to the one or more sensors in the sensor section 24 of the probe by any suitable conductors so as to carry the electrical signals from multiple sensors and thus permit electrical access to the probe from outside the patient's body. The multiple sensors can include a carbon dioxide sensor 40, an oxygen sensor 50, a thermocouple 47 and a pH-sensing electrode 58, or any combination thereof or other sensors. Preferably, at least the portion of the sleeve 20 that is placed inside the blood vessel, including the sensor section 24, is provided with a surface treatment 38 to inhibit the accumulation of thrombus, protein, or other blood components which might otherwise impair the blood flow in the vessel or impede the diffusion of oxygen or carbon dioxide into the sensing chambers 41 and 51. A preferred method for the application of such surface treatment is hereinafter described.

Figure 4:
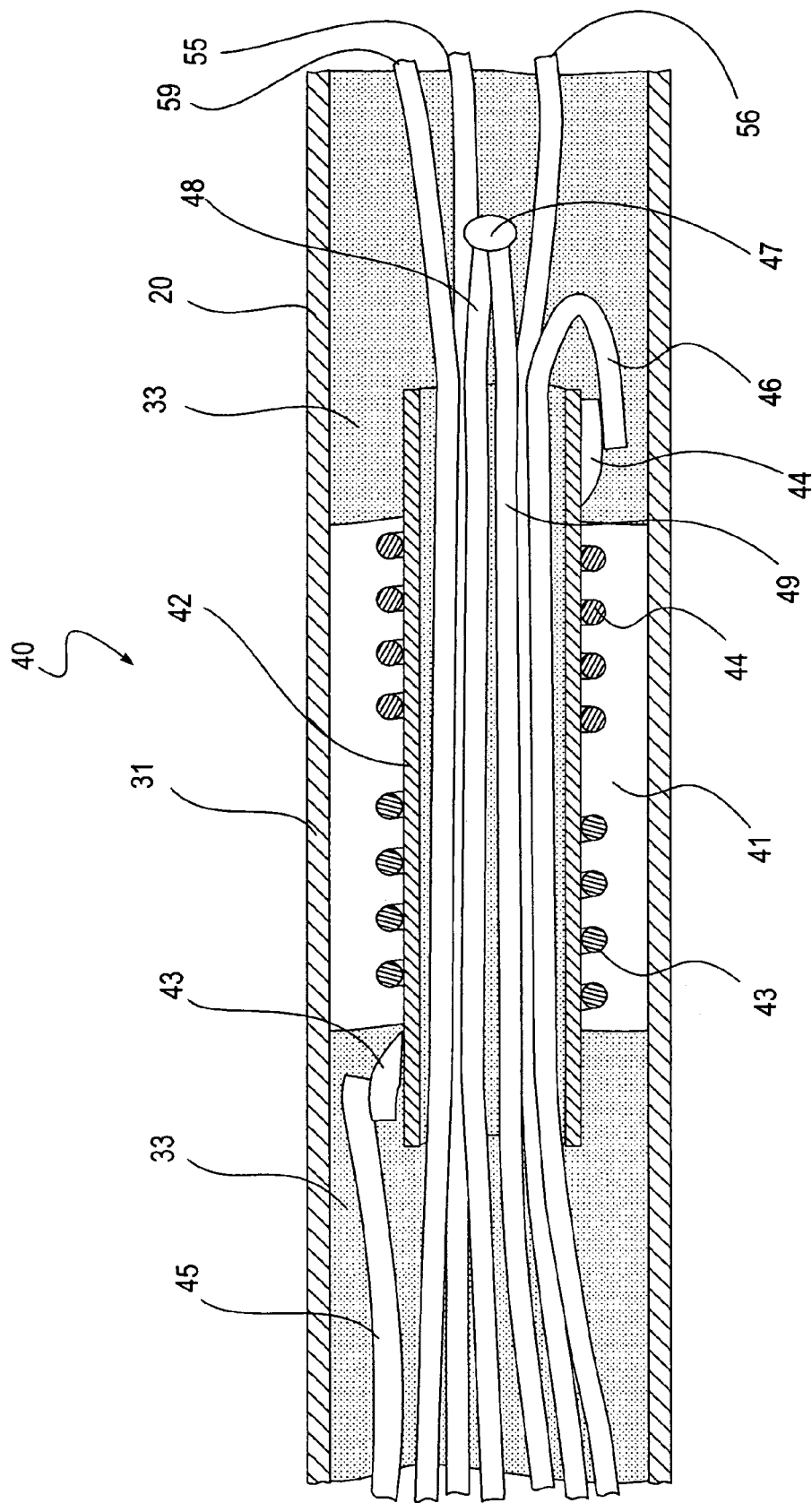
FIG. 4 is an enlarged cross-sectional view of the carbon dioxide sensor section of the probe of FIG. 1.

FIG. 4 provides a detailed view of one embodiment of the carbon dioxide sensor 40 contained within the sensor section 24 of probe 18. The carbon dioxide sensor 40 includes a chamber 41 containing an electrolyte solution and first and second electrodes 43 and 44. The sleeve 20 and the ultraviolet-cured adhesive 33, which seals each end of the chamber 41, define the chamber volume. The chamber 41 is preferably filled with an electrolyte solution such as 0.154 Molar NaCl (normal saline) with 0.001 Molar $NaHCO_3$ (sodium bicarbonate). The pH of this solution varies with the partial pressure of carbon dioxide, and the electrodes 43 and 44 generate an electrical potential in response to this pH. The reference electrode 43 for the carbon dioxide sensor preferably can be formed from a silver wire coated with silver chloride, produced by dipping a silver wire into molten silver chloride, or alternatively by a known electrochemical process. The sensing electrode 44 for the carbon dioxide sensor is a platinum wire coated with platinum dioxide, produced by sintering platinum dioxide powder onto the surface of a platinum wire, or alternatively, by an electrochemical or vapor deposition process. The electrodes 43 and 44 are attached or otherwise coupled to respective first and second electrical conductors 45 or 46, such as insulated copper wires, by soldering or welding.

Ideally, the carbon dioxide sensor 40 occupies a small axial length of the probe 18 in the range of 1 mm to 10 mm, but preferably 4 mm, so that the sensor section 24 of the probe 18 is short enough, such as less than 20 mm, but preferably less than 13 mm, to be easily advanced into a tortuous vessel. While occupying a small axial length of the probe 18, the carbon dioxide sensor design provides large electrode areas and maintains a large physical separation between the electrodes. Additionally, the carbon dioxide sensor provides a conduit for passage of the electrical conductors to the more distal electrodes of a multi-sensor probe, electrically isolated from the electrolyte solution inside the carbon dioxide sensor chamber 41. In the embodiment shown in FIG. 4, both the reference electrode 43 and the sensing electrode 44 are coiled around a tube 42, such as a polyimide tube having an outer diameter of 0.011 inch, an inner diameter of 0.009 inch, and a length of 8 mm. The coiled electrodes 43 and 44 provide large electrode surface areas in a small volume, and the two electrodes 43 and 44 are physically separated from each other by coiling the reference electrode 43 around the proximal half of the tube 42, while the sensing electrode 44 is coiled around the distal half of the tube 42 with a relatively large axial separation, such as 1 mm, between the two coils. Additionally, the inner lumen of the polyimide tube 42 provides a conduit for passage of the conductors for the more distal electrodes, electrically and physically isolated from the electrolyte solution in the sensor chamber 41 by multiple layers of insulation including the insulation on the electrical conductors themselves, the polyimide tubing, and the air or adhesive that fills the inner lumen of the polyimide tube 42. The polyimide tube 42 is anchored in the adhesive 33, which seals the ends of the sensor chamber 41, thereby providing additional mechanical strength to the carbon dioxide sensor section of the probe 18, beyond that provided by the sleeve 20 alone. The electrolyte solution of the carbon dioxide sensor 40 is contained in the annular space between the polyimide tube 42 and the sleeve or body 20 of the probe 18. The sleeve 20 can form a large surface area circumferential window 31 for the carbon dioxide sensor 40, which is not easily blocked by close proximity to a blood vessel wall.

FIG. 4 also shows a temperature sensing thermocouple 47 contained within the sensor section 24 of probe 18. The thermocouple 47 can include a pair of conductors 48 and 49 of dissimilar materials, electrically connected to each other by soldering or welding. The conductors are chosen from known pairs of materials, such as copper and constantan, with known responses to temperature. The thermocouple junction is electrically insulated from the other sensor electrodes, and it is embedded within the sensor section 24 of probe 18 in proximity to the other sensors where it will accurately reflect the temperature of the surrounding blood.

Figure 5:
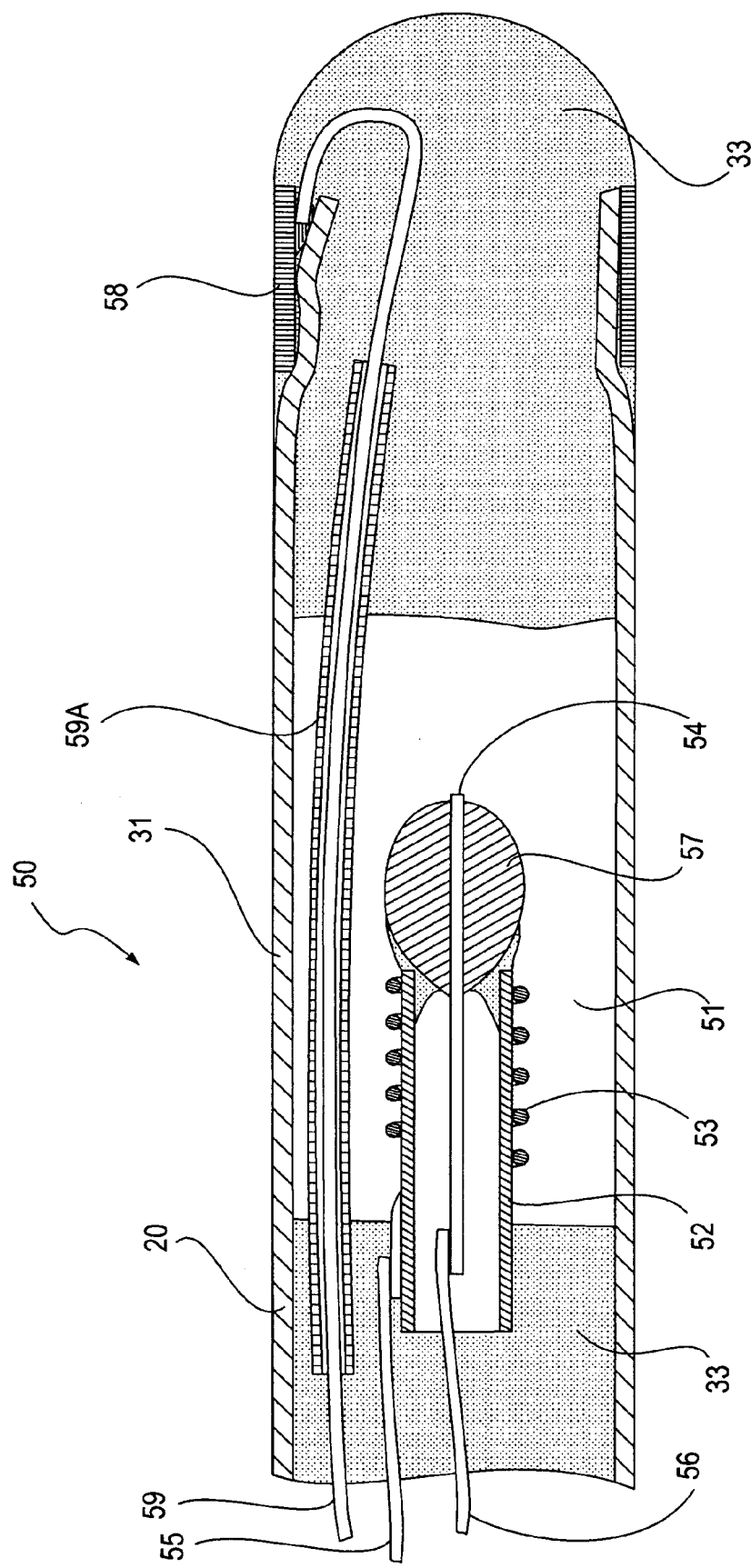
FIG. 5 is an enlarged cross-sectional view of the oxygen sensor section of the probe of FIG. 1.

FIG. 5 provides a detailed view of one embodiment of the oxygen sensor 50, which is contained within the sensor section 24 of probe 18. The oxygen sensor 50 can include a chamber 51 containing an electrolyte solution and third and fourth electrodes 53 and 54. The chamber 51 is defined by the sleeve 20 and ultraviolet-cured adhesive 33, which seals each end of the chamber. The chamber is preferably filled with an electrolyte solution, such as 0.154 Molar NaCl (normal saline) buffered with 0.120 Molar $NaHCO_3$ (sodium bicarbonate). With an appropriate electrical potential biasing the electrodes, such as 0.70 volts, a platinum electrode 54 serves as the catalyst for a chemical reaction that consumes oxygen and generates an electrical current in proportion to the rate of consumption of oxygen at the platinum electrode, which is in turn dependent on the partial pressure of oxygen in the blood surrounding the sensor 50. The sodium bicarbonate buffer stabilizes the pH of the electrolyte solution against changes that would be otherwise induced by the chemical reaction that consumes oxygen at the platinum electrode 54. When the buffer or electrolyte solution is exhausted, or when the sensor chamber 51 becomes filled with excessive silver chloride precipitate, the oxygen sensor response will change, and the sensor will no longer be viable. Probe 18 therefore advantageously provides a sufficiently large chamber volume filled with buffered electrolyte to provide the required lifetime for the oxygen sensor. The reference electrode 53 for the oxygen sensor 50 preferably consists of a silver wire coated with silver chloride, produced by dipping a silver wire into molten silver chloride, or alternatively by a known electrochemical process. The sensing electrode 54 for the oxygen sensor 50 is a platinum wire. The electrodes are attached or otherwise coupled to respective third and fourth electrical conductors 55 or 56, such as insulated copper wires, by soldering or welding.

Preferably, the oxygen sensor 50 occupies a small axial length of the probe 18 in the range of 1 mm to 10 mm, but preferably 4 mm, so that the sensor section 24 of the probe 18 is short enough, such as less than 20 mm, but preferably less than 13 mm, to be easily advanced into a tortuous artery. While occupying a small axial length of the probe 18, the oxygen sensor design should provide a large reference electrode area, maintain a large physical separation between the electrodes, and provide a large volume of electrolyte solution. Additionally, the sensing electrode 54 exposes only a small and well-defined surface area to the electrolyte solution. Additionally, the oxygen sensor provides a conduit for passage of the electrical conductors to the more distal electrodes of a multi-sensor probe, electrically isolated from the electrolyte solution inside the oxygen sensor chamber 51. In the embodiment shown in FIG. 5, the reference electrode 53 is coiled around a tube 52, such as a polyimide tube having an outer diameter of 0.007 inch, an inner diameter of 0.005 inch, and a length of 5 mm. The coiled reference electrode 53 provides a large electrode surface area in a small volume. The sensing electrode 54 is preferably formed from a short exposed length of a small diameter platinum wire, in the range from 0.001 inch to 0.008 inch, but preferably 0.002 inch in diameter.

Preferably, the sensing electrode 54 is formed by first oxidizing the surface of a small diameter platinum wire by heating in a furnace with an oxygen atmosphere, then fusing a bead 57 of sealing glass onto the platinum wire. The sealing glass is chosen to provide a coefficient of thermal expansion in the range from 8.0 to $9.2 \times 10^{-6}/° K$, but preferably $8.6 \times 10^{-6}/° K$, closely approximating or matched to the coefficient of thermal expansion for platinum, $9.0 \times 10^{-6}/° K$. The glass forms a strong bond to the platinum oxide on the surface of the platinum wire, and the matched thermal expansion coefficients minimize the thermal stress during cooling of the glass and platinum, thereby inhibiting cracking of the glass or separation of the glass from the electrode that could lead to drift in the oxygen sensor as the exposed platinum electrode area changes. The glass bead 57 forms a reliable seal to the platinum wire electrode 54, ensuring a stable platinum electrode area for drift-free operation of the device. The bond between the sealing glass and the oxidized platinum wire is much more tenacious and fluid-resistant than the bond formed by an adhesive used in prior oxygen sensor designs, rendering the present invention much more stable than a design based on an adhesive seal. Gluing the glass bead 57 into the end of the tube 52 and trimming the distal end of the platinum wire flush, or within one wire diameter of the tip of the glass bead 57 completes the oxygen electrode assembly. The two electrodes 53 and 54 are physically separated from each other because the reference electrode 53 is coiled around the tube 52 and the sensing electrode 54 is exposed only at the tip of the glass bead 57, separated from the reference electrode 53 by a relatively large axial separation such as 1 mm. Additionally, the oxygen sensor 50 includes a conduit 59A, preferably formed from polyimide or other insulating tubing, for passage of the conductor 59 leading to the more distal pH-sensing electrode 58. The conductor 59 is electrically and physically isolated from the electrolyte solution in the sensor chamber 51 by multiple layers of insulation including the insulation on the electrical conductor 59, the insulating tubing conduit 59A, and the air or adhesive that fills the inner lumen of the conduit 59A. The electrolyte solution of the oxygen sensor 50 is contained in the annular space between the polyimide tube 52 and the sleeve 20, and in the cylindrical space beyond the tip of the glass bead 57 and the platinum sensing electrode 54. The sleeve 20 preferably forms a large surface area circumferential window 31 for the oxygen sensor 50, which is not easily blocked by close proximity to a blood vessel wall.

FIG. 5 also shows a detailed view of the pH sensor contained within the sensor section 24 of probe 18. The pH sensor includes a noble metal electrode 58, such as a gold or platinum band, mounted on the external surface of the probe 18 where it is directly exposed to the blood, and a reference electrode 43 or 53. The reference electrode for the pH sensor preferably consists of a silver wire coated with silver chloride, produced by dipping a silver wire into molten silver chloride, or alternatively by a known electrochemical process. The reference electrode 43 or 53 can be shared with the oxygen sensor 40 or the carbon dioxide sensor 50. The pH-sensing electrode 58 is attached to an electrical conductor 59, such as an insulated copper wire, by soldering or welding.

Figure 6A:
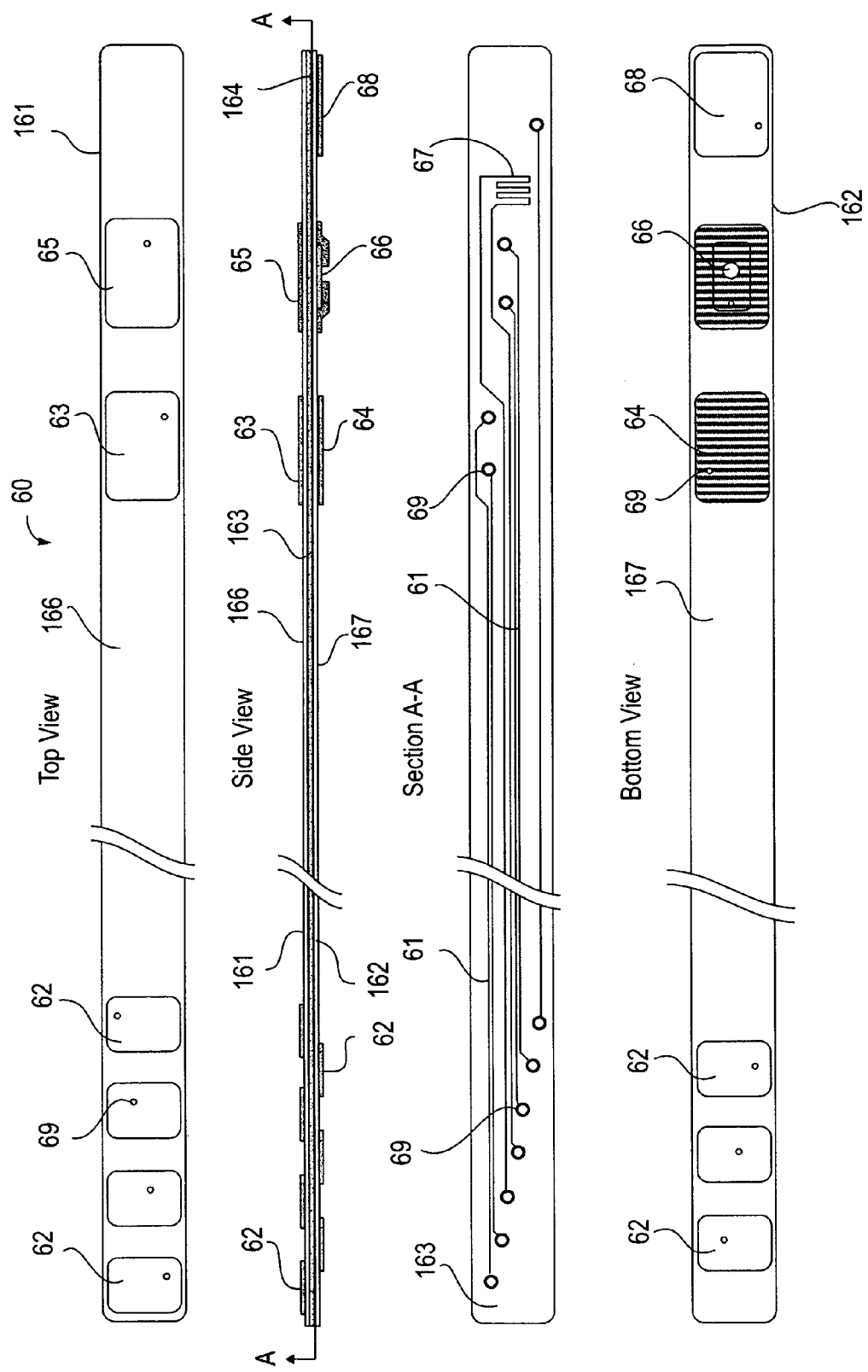
FIG. 6A are several views of a flexible circuit subassembly of another embodiment of the probe of FIG. 1.

As hereinbefore described, the probe is generally constructed from various wires, tubes, and electrodes, inserted into a bore of a tubular sleeve 20, which is subsequently filled with adhesive and electrolyte solutions to form the sensors. In an alternative embodiment, a flexible circuit replaces the wires, tubes, and electrodes. The flexible circuit can be mass-produced in a batch process at low cost, thereby minimizing the cost of the multi-sensor probe. FIG. 6A shows a flexible circuit 60 which incorporates all of the electrical elements of a multi-sensor blood gas sensor probe, including electrical contact pads 62 comprising a low profile electrical connector 22, electrical conductors 61, and sensing electrodes 63 through 68 of various types, all fabricated on a flexible planar substrate having three layers of circuitry separated by two layers of flexible insulating substrate such as polyimide. Such a flexible circuit can be manufactured using a known batch process wherein successive layers of conducting materials on insulating substrates are deposited by electroplating, vapor deposition, or other methods, then patterned by photolithography, laser ablation, or other methods. The patterned layers are bonded together with an insulating adhesive to complete the multi-layer flexible circuit. Once the processing steps have been completed, individual circuits are cut into narrow strips having a width such as 0.015 inch, such that the circuit can be inserted into a sleeve 20 and filled with adhesive 33 and electrolyte solutions to form the sensor chambers 41 and 51 over the electrode sections of the flexible circuit 60.

The flexible circuit 60 has a length, such as 25 cm, appropriate for the circuit to be situated longitudinally within the lumen of a sleeve and can have a width ranging from 0.008 inch to 0.030 inch and preferably 0.015 inch. The proximal end or portion of the flexible circuit 60 preferably has at least two pads 62, and more preferably seven pads 62, which serve as the electrical contacts 32 for a low profile electrical connector 22. The connector pads 62 are plated with gold to provide reliable electrical contact with the mating connector 15 of the display module 12. The contact pads are connected to traces or conductors 61, sandwiched or disposed between first and second insulating layers 161 and 162 of the flexible circuit substrate and more specifically formed one or both of the inner surfaces 163 and 164 of respective layers 161 and 162. The traces 61 are in turn connected to a plurality of pads 63-66 and 68 near the distal end or portion of the flexible circuit 60, which serve as electrodes for the various sensors. The pads and traces of the flexible circuit 60 are primarily formed of copper, and the pads are plated with various metals including silver, platinum, and gold to create the electrodes of the various sensors. The pads 62, 63-66 and 68 on one or both of the exposed outer surfaces 166 and 167 of the flex circuit are connected to traces 61 by feedthrough vias 69 or any other suitable means. The reference electrodes 63 and 65 for the oxygen, carbon dioxide, and pH sensors are preferably formed by subjecting silver-plated pads to a known electrochemical process wherein the silver is reacted with chloride ions in a solution to form a layer of silver chloride on the surface of the silver. The sensing electrode 64 for the carbon dioxide sensor is preferably formed by subjecting a platinum-plated pad to a known electrochemical process wherein the platinum metal is reacted in a platinum chloride solution to form a platinum dioxide layer on the surface of the platinum. The sensing electrode 66 for the oxygen sensor is preferably formed by masking a platinum-plated pad electrode with an insulating material to define a small exposed area of platinum metal in the range from 0.001 inch to 0.008 inch in diameter, but preferably 0.002 inch in diameter. The pH-sensing electrode 68 is preferably a gold-plated or platinum-plated pad, directly exposed to the blood. The flexible circuit 60 can further accommodate a temperature sensor in the form of a patterned thin film of known material, forming a temperature-sensitive resistor 67 on inner surface 163 of first layer 161. Alternatively, the temperature sensor can be a diode, thermistor, or thermocouple, bonded to one of the flexible circuit substrate layers 161 and 162.

Figure 6B:
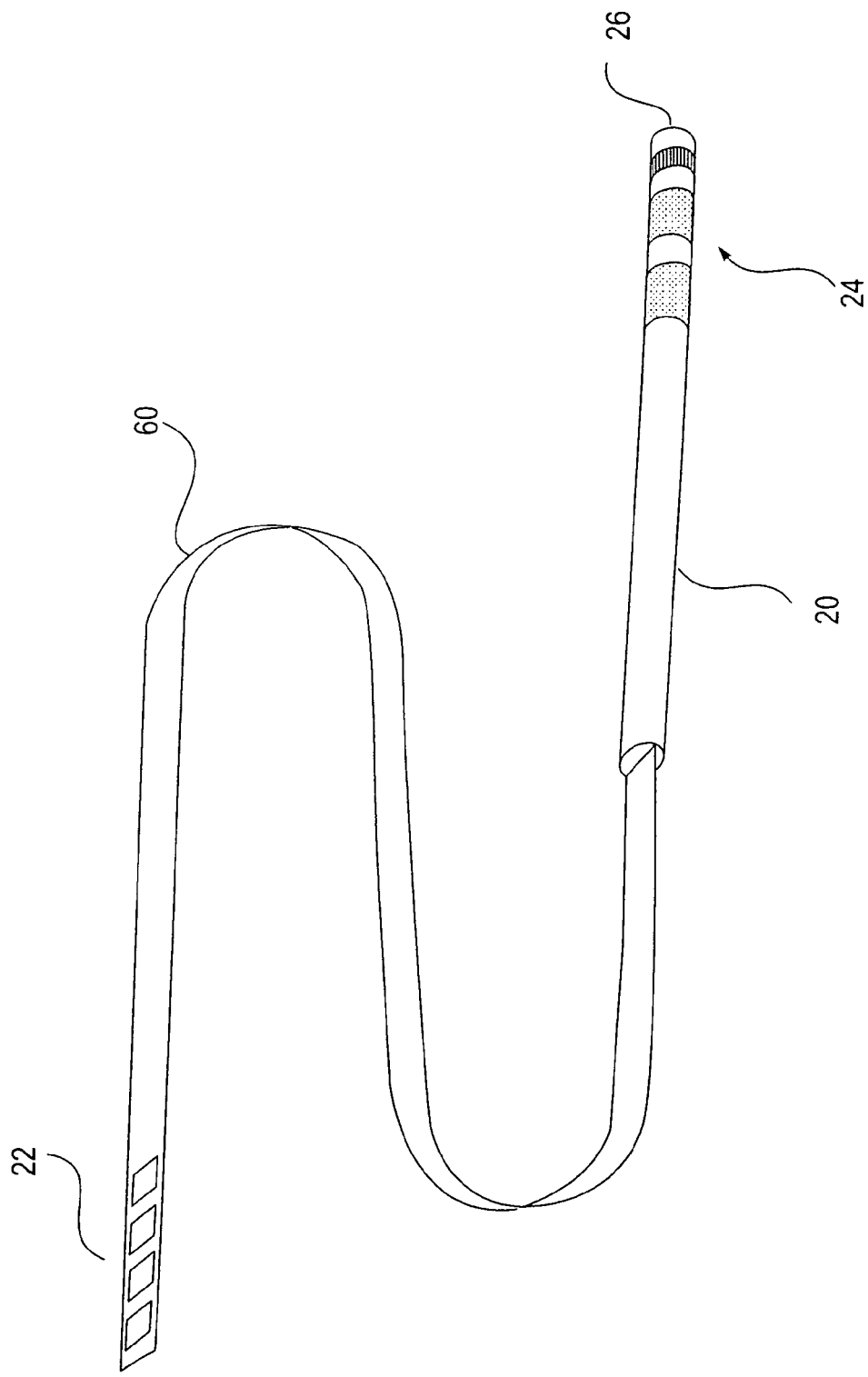
FIG. 6B is an isometric view of the probe of FIG. 1.

FIG. 6B shows the flexible circuit 60, including various electrodes, inserted into the lumen or bore of the sleeve 20, which is preferably sealed with adhesive 33 and filled with electrolyte solutions to form the internal chambers 41 and 51 of the carbon dioxide and oxygen sensors. The proximal end or portion of the flexible circuit 60 includes buried traces, which serve as electrical conductors 61, and gold-plated pads, which serve as electrical contacts 62 for the electrical connector 22. The buried traces conduct electrical signals from the sensor electrodes 63 through 68 to the electrical contacts pads 62, which serve as a low profile electrical connector 22 that can be coupled to the mating connector 15 of the display module 12.

As hereinbefore described, at least the portion of the polymer sleeve 20 that forms the external surface of the probe 18 is preferably provided with a durable surface treatment 38 to inhibit the accumulation of thrombus, protein, or other blood components, which might otherwise impair blood flow in the artery or impede the transport of oxygen or carbon dioxide through the circumferential window 31 into the sensing chamber 41 or 51 (see FIG. 3). One preferred method for treating the surface of the sleeve 20 is photoinduced graft polymerization with N-vinylpyrrolidone to form a dense multitude of microscopic polymerized strands of polyvinylpyrrolidone, covalently bonded to the probe outer surface. This surface treatment 38 is durable, due to the strong covalent bonds, which anchor the polymer strands to the underlying substrate. The surface treatment 38 adds only a sub-micron thickness to the probe body 20, yet it provides a hydrophilic character to the probe surface, rendering it highly lubricious when hydrated by contact with blood or water, thereby facilitating the smooth passage of the probe 18 through the blood vessel. This hydrophilic surface treatment 38 also inhibits the adsorption of protein onto the surface of the underlying polymer substrate, thereby minimizing the accumulation of thrombus, protein, or other blood components on the probe 18. Although the dense multitude of polyvinylpyrrolidone polymer strands shields the underlying outer wall of the sleeve or cannula 20 from large protein molecules, it does not significantly impede the migration of small molecules such as oxygen or carbon dioxide through the wall of the cannula. Therefore, the surface treatment 38 of the polymethylpentene sleeve 20 facilitates consistent, reliable communication of the gases in the blood, such as oxygen and carbon dioxide, through the circumferential window 31 into the oxygen and carbon dioxide sensor chambers 41 and 51, even after prolonged residence time up to three days in the bloodstream of a patient.

Figure 7:
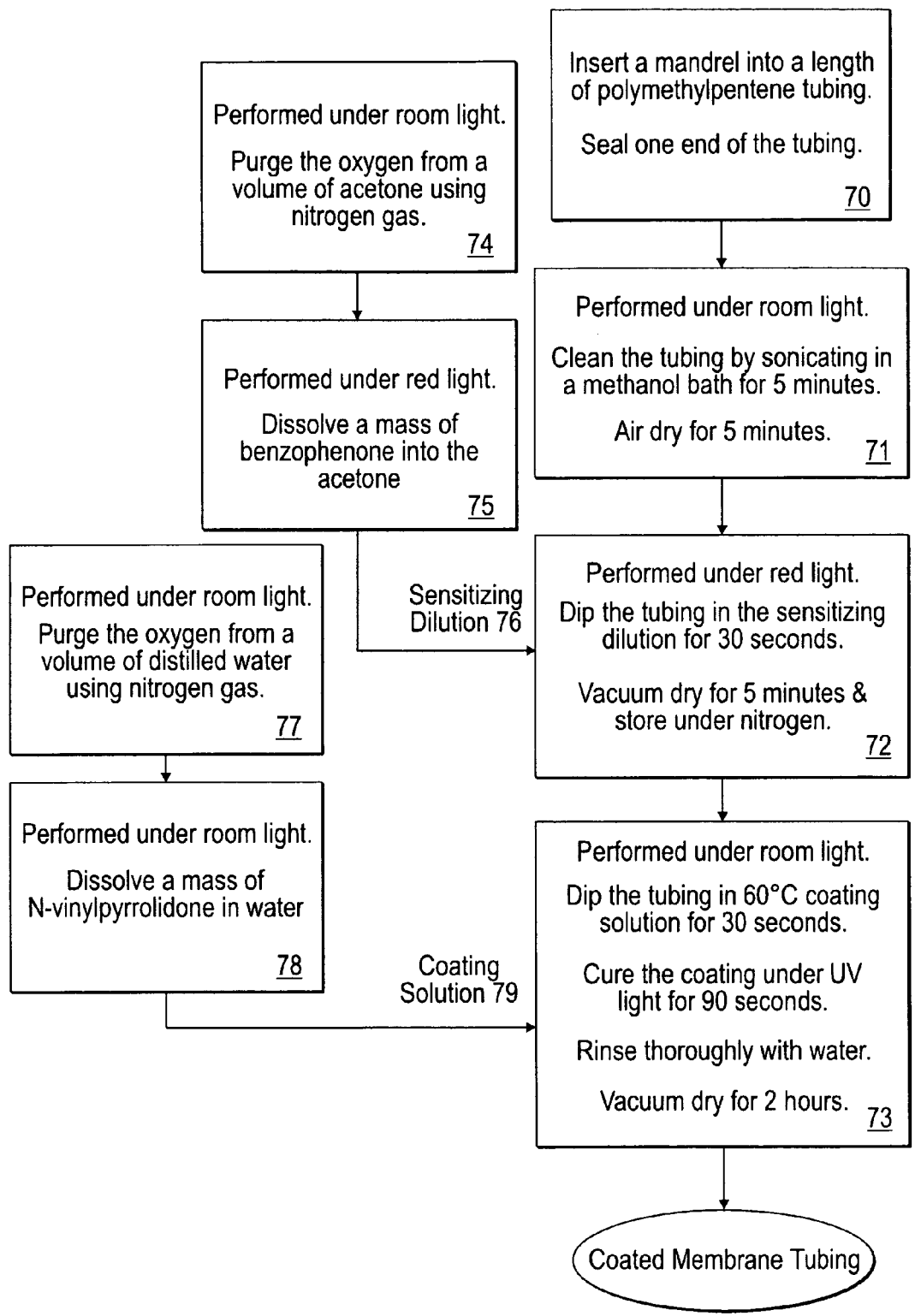
FIG. 7 is a flowchart of the surface treatment process for the probe of FIG. 1.

One procedure for surface treatment of the polymer sleeve material is described hereinafter and is shown as a flowchart in FIG. 7. In preparation for the surface treatment process, two solutions are prepared, the sensitizing dilution 76 and the coating solution 79. The sensitizing dilution 76 is prepared in two phases. In a first phase or step 74, performed under room light illumination, a blanket of nitrogen gas is applied to a volume of acetone, preferably 90 ml of acetone, after the acetone has been purged with nitrogen gas for a duration such as five minutes. In a second phase or step 75, performed under red light illumination, a mass of benzophenone, preferably 1.0 g of benzophenone, is dissolved in the acetone, with additional acetone added to the solution to make up a total volume of 100 ml. The coating solution 79 is prepared in two phases, both of which are carried out under room light illumination. In the first phase or step 77, a blanket of nitrogen gas is applied to a volume of distilled water in a flask, preferably 80 ml of distilled water, after the distilled water has been purged with nitrogen gas for a duration such as five minutes. In the second phase or step 78, while the nitrogen gas is still being applied, a mass of N-vinylpyrrolidone, preferably 11.4 grams of N-vinylpyrrolidone, is dissolved in the distilled water. The flask is capped and the coating solution 79 is ready for storage or application.

A membrane tubing assembly is prepared for surface treatment in step 70 by placing a mandrel inside a polymethylpentene tube of the proper length and sealing one end of the tube. In a preliminary phase or step 71 of the surface treatment procedure, performed under room light illumination, the membrane tubing assembly is immersed in methanol and sonicated for five minutes to thoroughly clean the outer surface, then allowed to air dry for five minutes. In a second phase or step 72 of the surface treatment procedure, performed under red light illumination, the membrane tubing assembly is dipped into a sensitizing dilution 76 of benzophenone in acetone for 30 seconds, under a nitrogen purge. The sensitized membrane tubing assembly is then removed and placed in a dessicator, still under red light illumination, dried for a duration such as five minutes under partial vacuum such as 28 mmHg, and stored in an amber vial with a nitrogen blanket. In a third phase or step 73 of the surface treatment procedure, performed under room light illumination, the sensitized membrane tubing assembly is dipped in a volume of the N-vinylpyrrolidone coating solution 79, such as 30 ml of solution, that has been heated to 60° C. The coating is cured by exposure to ultraviolet curing lights for a period such as 90 seconds, during which time the N-vinylpyrrolidone is polymerized to form a multitude of polyvinylpyrrolidone strands, covalently bonded to the membrane tubing substrate. The membrane tubing assembly is rinsed with copious amounts of distilled water, then placed in a dessicator to be dried under vacuum such as 28 mmHg for a period such as two hours to complete the preparation of the surface treated membrane tubing.

The surface treated polymethylpentene tubing may be used as the sleeve 20 in the manufacture of a complete probe assembly, which will then retain the beneficial properties of the N-vinylpyrrolidone surface treatment. Alternatively, the probe assembly 18 can be manufactured using untreated tubing, and the surface treatment can be subsequently applied to the completed probe 18 using substantially the same method as describe hereinbefore.

The display module 12, as shown in FIG. 1, includes a housing 17 formed of a suitable material such as plastic and which is sized so that it can be worn on the patient, such as on the patient's wrist, arm or other limb, sometimes referred to herein as the subject, with the probe(s) 18 inserted into vessel (s) in the hand, wrist, or forearm. The module 12 also includes a display 13 such as a liquid crystal display (LCD) for displaying measured parameters and other information, and adapted to be readily visible to the attending medical professional, sometimes referred to herein as the user. The display 13 may include backlighting or other features that enhance the visibility of the display. The band 14 attached to the housing 17 is adapted to secure the display module 12 to the subject's wrist. Alternatively, the module 12 may be attached to the subject's arm or to a location near the subject. Optionally, in the case the subject is a newborn infant (neonate), the module 12 may be strapped to the subject's torso, with the probe(s) 18 inserted into umbilical vessel(s). The band 14 is comprised of any suitable material, such as Velcro, elastic, or the like. Buttons 16 or keys facilitate entry of data and permit the user to affect the display 13 and other features of the module 12. While FIG. 1 shows three buttons, any number or type of buttons, keypads, switches or the like may be used to permit entry of parameters or commands, or to otherwise interface with the apparatus 10. The module 12 may also include wireless communications capability to facilitate display of physiologic parameters on a remote monitor or computer system, and/or to facilitate the entry of patient parameters or other information into the module 12 from a remote control panel or computer system. The module 12 also includes one or more connectors 15 that provide physical connection and communication with one or more probes 18. Preferably, each connector 15 includes a receptacle adapted to receive, secure, and communicate with a corresponding connector 22 on the proximal end of the probe 18.

Figure 10:
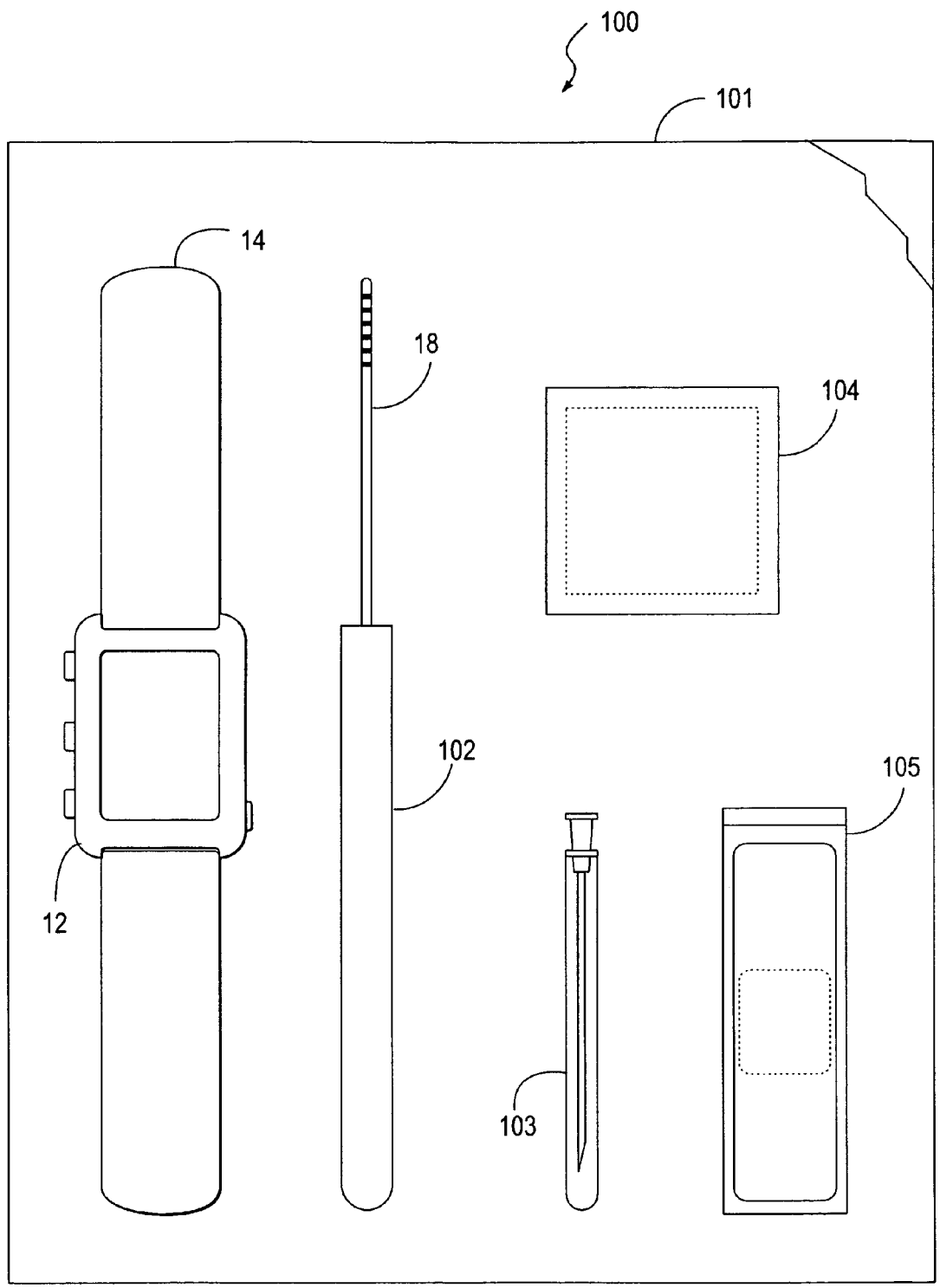
FIG. 10 is a plan view, partially cut away, of a kit of the present invention.

In a preferred embodiment of the display module 12, the module is designed to be low in cost so that it can be packaged together with a probe(s) 18 and accessories as a disposable kit 100, with all of the components of the kit packaged together in a sterile pouch or other container 101, as illustrated in FIG. 10. In addition to the display module 12 and probe(s) 18, the kit would optionally include a probe holder 102 to protect the probe from damage or degradation, a wrist band 14 or other means for attaching the display module to a patient, a needle or other introducer 103, alcohol swabs 104 for cleaning the skin prior to cannulating the vessel and for cleaning blood or other residue from the probe connector prior to attaching the probe to the module, a bandage 105 to cover the puncture site and anchor the probe in place, and any other items that may be utilized for preparing and using the probe 18 and display module 12. The display module 12 is further designed to require low power so that it can operate for the expected lifetime of the device, such as 72 hours, on battery power without the need for battery replacement or connection to an external power source. The probe 18 is preferably suited to be a single-use, disposable device, since it has a limited operational lifetime and is used in direct contact with the subject's blood. The module 12 is durable enough to be used many times, however, the advantage of a disposable module is that it eliminates the expense and the infection hazard associated with cleaning, replacing batteries, and reusing a single module for multiple patients. An additional advantage of a disposable module 12 packaged together with its associated probe(s) 18 is that the calibration data can be stored in the module at the time of manufacture, greatly simplifying the use of the apparatus 10 by eliminating the need for the user to enter calibration data into the module prior to using the probe 18. An additional advantage of a disposable module 12 packaged together with its associated probe(s) 18 is that the calibration data stored in the module at the time of manufacture can account for all of the monitor and probe inaccuracies and artifacts in a single set of calibration coefficients, thereby avoiding the accumulation of inaccuracies that can occur with separate calibrations of the probe 18 and the module 12. In a preferred embodiment of the module, no user inputs at all are required, eliminating the need for buttons, keypads, switches, and the like. The display module 12 is automatically energized upon connection of the probe 18 to the module 12, and all of the calibration data and other needed information is pre-programmed into the module at the time of manufacture.

Figure 8:
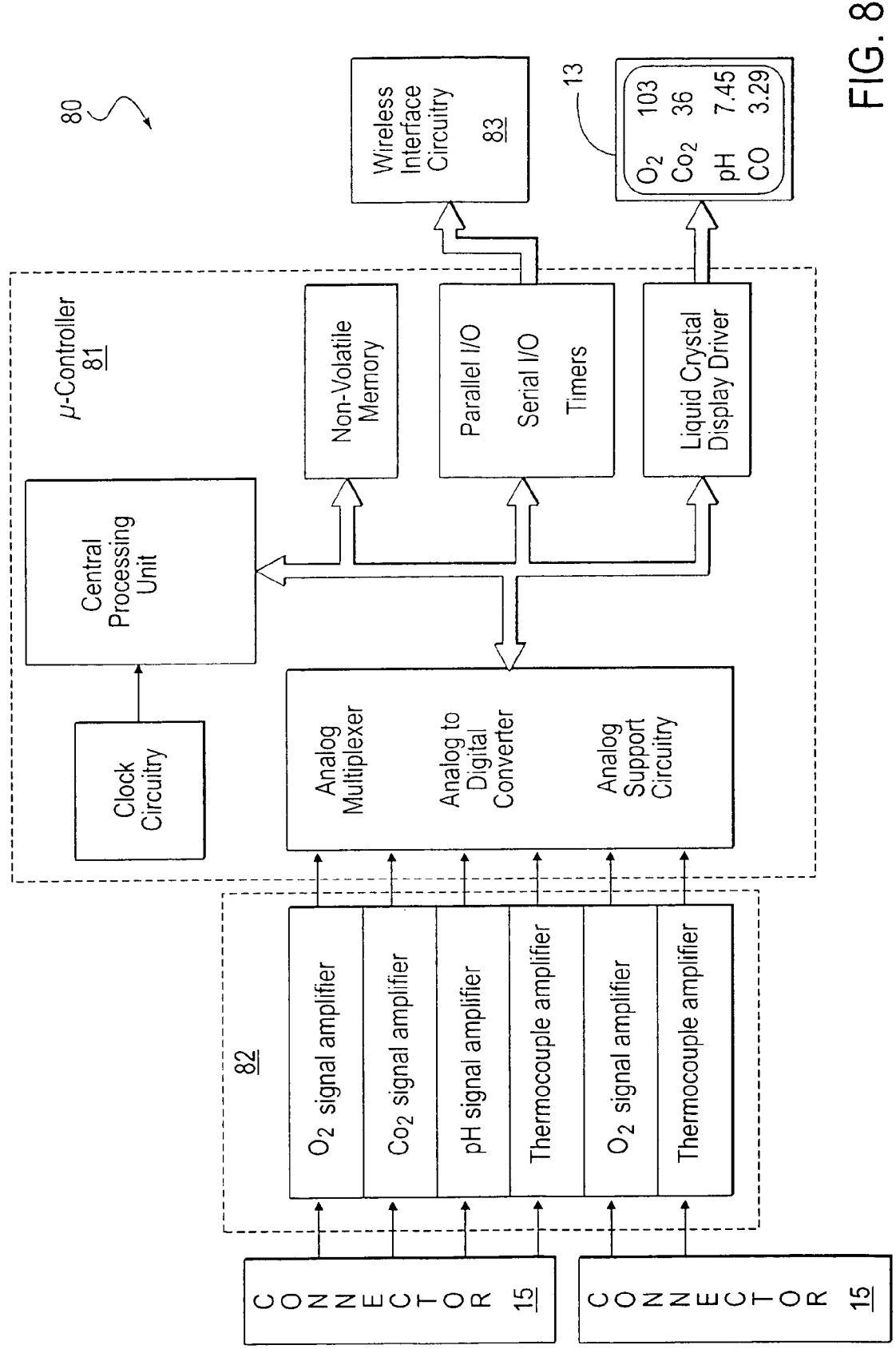
FIG. 8 is a block diagram of the circuitry contained in the display module of FIG. 1.

One embodiment of the electronic circuitry 80 included in the display module 12 is shown in block diagram form in FIG. 8. As shown therein, signals from the one or more sensors provided on the one or more probe(s) 18 arrive at the display module 12 via connector(s) 15. The sensor signals are received by a respective plurality of analog signal conditioning circuits 82, one for each sensor in the associated probe(s) 18. The outputs from the analog signal conditioning circuits 82 are directed to a microcontroller 81, such as the Texas Instruments MSP430F435, which includes many of the circuit elements required by the display module 12. In particular, the microcontroller 81 includes an analog multiplexer and an analog-to-digital converter to digitize the analog signals from the plurality of analog signal conditioning circuits 82, as well as analog support circuitry including a voltage reference, a temperature sensor, and power supply monitoring circuitry. In one preferred embodiment, the algorithm for processing the signals, together with the sensor and module calibration coefficients, is embedded in software stored in non-volatile memory included in the microcontroller 81. The microcontroller 81 further includes a central processing unit to execute the software algorithm and other peripheral functions including clock circuitry, serial and parallel input/output interfaces, timers, and the LCD driver circuitry. The LCD driver circuitry supplies the waveforms for the liquid crystal display 13, and the display module 12 can also communicate with an external computer or module over a serial data link via an optional wireless interface circuit 83 or other suitable means. The integration of most of the required functions of the display module circuitry into a single, inexpensive, low-power component, that is the microcontroller, makes it feasible to manufacture the module as a low cost, battery-powered disposable unit.

Each of the analog signal conditioning circuits 82 is adapted to the particular type of sensor to which it is connected. For the oxygen sensor, the analog signal conditioning circuit can be a current-to-voltage converter with a full-scale input current that includes the maximum full-scale current expected for the oxygen sensor, such as 100 nanoamps, and a full-scale output voltage matched to the analog-to-digital converter input range. The input bias current for the oxygen sensor circuit is preferably much less than the normal sensor operating current, such as an input bias current of less than 100 picoamps. For the carbon dioxide or pH sensor, the analog signal conditioning circuit can be a voltage amplifier with very high input impedance, such as greater than 1012 ohms, and very low input bias and input offset currents, such as less than 100 femtoamps. The circuit can include a fixed gain and offset voltage chosen to translate the full-scale sensor voltage range to match the analog-to-digital converter input range. The carbon dioxide or pH sensor circuit requirements may be satisfied by an instrumentation amplifier or by a simpler operational amplifier circuit, with the amplifier selected to provide the required low input bias and offset currents. For the thermocouple temperature sensor, the analog signal conditioning circuit can be a high gain voltage amplifier with an input voltage range of zero to 2 millivolts over the expected temperature range, and an output voltage to match the analog-to-digital converter input range. For the required high gain thermocouple signal conditioning circuit, the amplifier is preferably chosen to provide an input offset voltage much less than the signal voltage, such as an input offset voltage of less than 10 microvolts.

Figure 9:
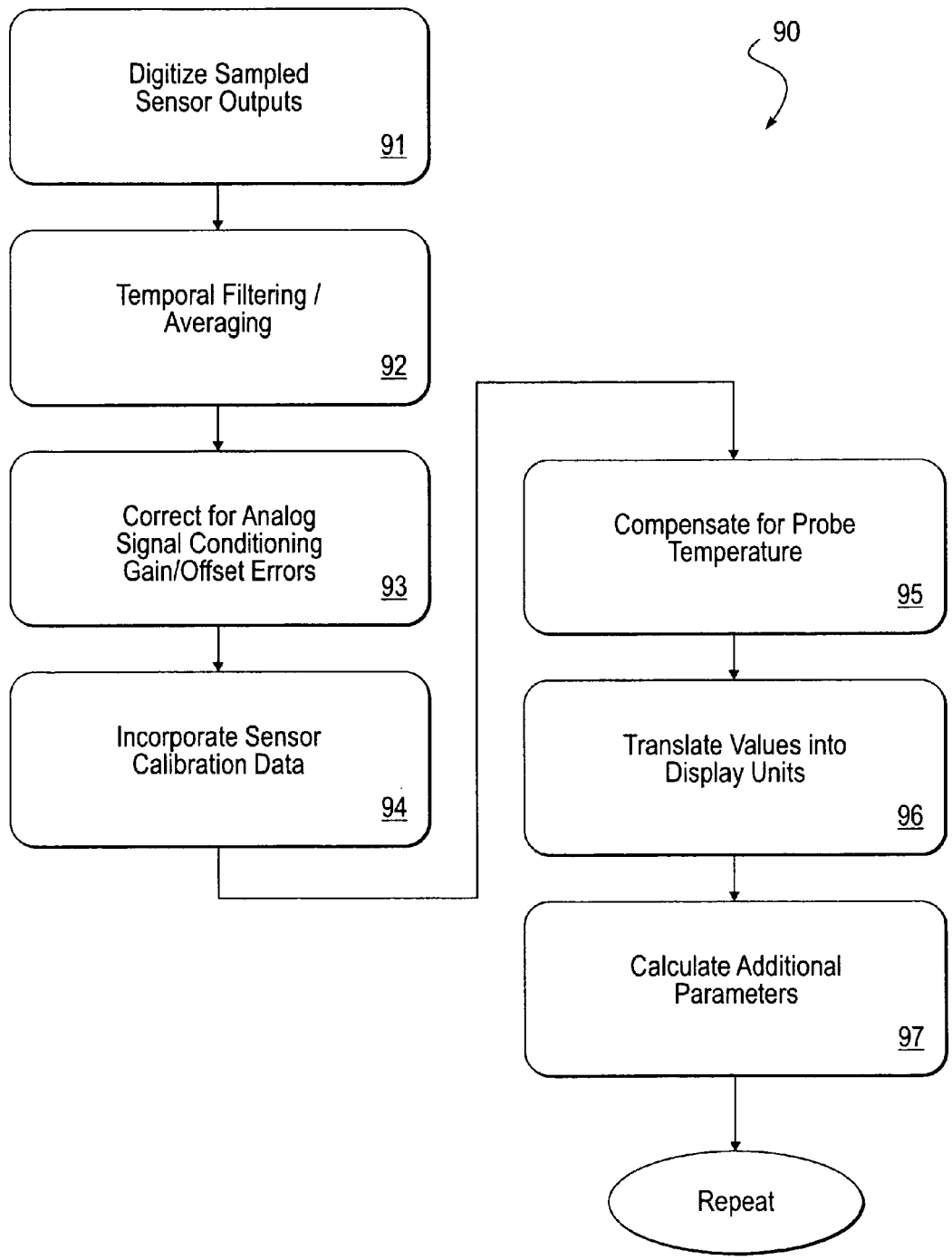
FIG. 9 is a flowchart of the processing algorithm to translate the sensor input signals into displayable values performed by the display module of FIG. 1.

One processing algorithm 90 that can be performed by the microcontroller 81 to convert the digitized sensor signals into displayable numeric values is shown in block diagram form in FIG. 9. The processing algorithm includes the steps of digitizing the sampled sensor outputs in step 91, temporal filtering or averaging to reduce the noise from external interference or other sources in step 92, correcting for gain or offset errors in the analog signal conditioning circuitry in step 93, incorporating gain, offset, and linearity corrections from the sensor calibration data in step 94, compensating for the temperature dependence of the gain, offset and linearity of the sensor according to the measured probe temperature in step 95, and translating the value into the desired units for display on the LCD in step 96. In practice, if the module 12 and probe 18 are calibrated together as a single disposable apparatus, then all of the gain, offset, nonlinearity, temperature, and unit conversion factors from steps 93, 94, 95, and 96 can be incorporated into a single set of calibration functions that permit the direct translation of filtered analog inputs into displayable values without the need to calculate any intermediate corrections, and without the accumulation of errors from separate calibrations of the individual components of the apparatus. Optionally, the algorithm may include step 97 of calculating other physiologic parameters according to known formulas, possibly combining readings from multiple sensors, or combining multiple readings from a single sensor to provide additional useful information.

An example of a calculation based on a single reading from a single sensor is the estimation of arterial or venous oxygen saturation ($SaO_2$ or $SvO_2$) from the corresponding measured partial pressure of oxygen ($PaO_2$ or $PvO_2$). There is a known nonlinear relationship between the oxygen saturation and the partial pressure of oxygen in blood, but the saturation value is useful for calculating cardiac output and for other assessments of patient status.

An example of a calculation based on multiple readings from a single sensor is the determination of the trend in the associated blood gas parameter, that is, whether the value is increasing, decreasing, or stable. The trend in the blood gas parameter can be symbolically indicated on the display, making it easier for the user to quickly assess patient status.

An example of a calculation based on combined readings from multiple sensors is the use of the carbon dioxide reading and the pH measurement to calculate the bicarbonate level. According to a known relationship, the log of the bicarbonate concentration is equal to the pH, plus the log of the partial pressure of $CO_2$, minus the constant 7.608. This equation is appropriate for blood at 37° C., and it may be further compensated for temperature deviation from normal.

An example of a calculation based on combined readings from multiple sensors on multiple probes is the use of an arterial oxygen reading and a venous oxygen reading to estimate the cardiac output using a modified version of the Fick oxygen consumption method. According to the Fick method, cardiac output (liters/minute) is calculated as the oxygen consumption (milliliters/minute), divided by the arteriovenous oxygen concentration difference (milliliters of $O_2$ per liter of blood). For the present invention, oxygen consumption is estimated as 3 milliliters/kilogram times the subject's weight, which can be entered into the module by way of the buttons or keys, or by way of a wireless communication from an external computer or control panel. Assuming standard values for hemoglobin (12.5 grams/deciliter) and the oxygen carrying capacity of hemoglobin (1.36 milliliters of $O_2$ per gram of hemoglobin), the arteriovenous oxygen concentration difference can be calculated as the difference between the arterial oxygen saturation and the venous oxygen saturation ($SaO_2$—$SvO_2$) times the standard value of 170 milliliters of $O_2$ per liter of blood. In this calculation, the value of the venous oxygen saturation may be adjusted to compensate for the experimentally determined discrepancy between the pulmonary artery oxygen saturation and the forearm venous oxygen saturation.

The incorporation of wireless interface circuitry into the display module is advantageous in preserving the electrical safety and freedom of movement of the patient afforded by the self-contained, battery-powered display unit, while providing the benefits of an integrated system in terms of centralized data collection. The compact display module of the present invention makes the most of the wireless communications by freeing the subject from the tubes and cables that normally tether them to their bed, and by eliminating the need for additional bulky instrumentation at the already crowded bedside.

From the foregoing it can be seen that the apparatus 10 and method of the present invention makes it possible to measure blood gases of a subject, such as oxygen and carbon dioxide, as well as other blood parameters including temperature and pH. As hereinbefore described, a single probe may include more than one sensor, e.g., an oxygen sensor, a carbon dioxide sensor, a temperature sensor, and a pH sensor. The sensors are included in a probe body, having a small diameter of less than 0.023" so that it can be readily inserted through a 20-gauge needle into a blood vessel in the hand, wrist, or forearm. This probe includes at least one sensor with a window 31 having a large surface area and high permeability to the target gas molecules, which facilitates the rapid diffusion of blood gases into or out of the sensor chamber to ensure a fast response to changes in the blood gas concentration. The probes utilized are preferably blunt tipped and atraumatic to the vessel wall and are preferably provided with an antithrombogenic surface treatment to inhibit the formation of thrombus or the adhesion of protein or other blood components, ensuring consistent performance of the blood gas sensors and minimizing the need for continuous infusion of heparin to maintain a clot-free environment. The probe carries electrical signals from the sensors, through electrical conductors, to a low profile or other connector removably attached to a mating connector on the display module. The low profile of the preferred connector facilitates the removal of the hypodermic needle or other introducer used to most simply introduce the probe into the lumen of a vein or artery, thereby eliminating the need for using a split sheath introducer or other more complex technique for introducing the probe into the vessel. The display module is small and inexpensive, and it is particularly suited for attachment to the patient's wrist. The apparatus and method herein described may be adapted to the particular requirements of a variety of different medical applications, several of which are outlined below.

For patients in the intensive care unit (ICU) or coronary care unit (CCU), there is typically the need for monitoring arterial blood gases (oxygen and carbon dioxide) and pH. Currently, this monitoring is performed on an intermittent basis, typically three to twelve times per day, by drawing a blood sample from an arterial line in the patient's forearm, and delivering the blood sample to a blood gas analyzer. A multi-sensor probe as described herein, providing continuous oxygen, carbon dioxide, and pH measurements, can eliminate the need and the associated expense and risks of placing and maintaining an arterial line and repeatedly drawing blood samples therefrom. Furthermore, the continuous monitoring provided by the present invention gives rapid feedback regarding the effects of any interventions such as adjustments to the ventilator settings or administration of drugs. The timely feedback on the effects of the medical interventions permits the subject to be more quickly weaned from the ventilator and released from the ICU/CCU, a benefit to the both the patient and the healthcare system.

In a subset of ICU/CCU patients, where there is a need to monitor cardiac output, the addition of a venous oxygen sensor probe to the previously described multi-sensor arterial probe, makes it possible for the present invention to estimate the cardiac output using a modified arteriovenous oxygen concentration difference equation (the Fick method) as hereinbefore described. Currently, cardiac output is most frequently monitored using the thermodilution technique, which requires placement of a Swan-Ganz catheter in the jugular vein, through the right atrium and right ventricle, and into a branch of the pulmonary artery. The thermodilution technique requires injections of cold saline boluses at intervals, whenever a cardiac output reading is desired. The replacement of the right heart catheter with the present invention greatly reduces the risk to the patient by eliminating the right heart catheterization procedure, and it provides greater utility by providing on demand cardiac output readings without cumbersome injections of cold saline.

In another subset of ICU/CCU patients, where there is a need to frequently monitor cardiac output but not arterial blood gases, a simpler apparatus is a single venous oxygen probe used to monitor the venous oxygen content. This value is combined with independent measurements of arterial oxygen saturation from a noninvasive pulse oximeter, hemoglobin density from a daily blood sample, and calculated oxygen consumption according to the standard approximation based on weight and height, to calculate cardiac output according to the Fick method. The probe is placed in a vein in the hand, using an experimentally determined compensation factor to account for the expected difference between the oxygen saturation in the right atrium and the oxygen saturation in a vein of the hand. Alternatively, the oxygen probe can be inserted directly through the jugular vein in the neck, into the vena cava or the right atrium of the heart to provide a direct measurement of the oxygen saturation of the mixed venous blood without the need for a compensation factor. Besides its utility for estimating cardiac output, the venous oxygen content is a valuable parameter on its own for assessing the status of the patient.

In neonates, there is frequently the need for arterial and venous blood gas monitoring, along with the measurement of cardiac output and other blood parameters. The present invention is particularly suitable for neonates, since it minimizes if not eliminates the need for drawing blood from the neonate subject with a small blood volume to draw from. The addition of hemoglobin, bilirubin, electrolyte, or glucose sensors to the blood gas and pH sensors increases the utility of the multi-sensor probe for this application. The probes are conveniently inserted into umbilical arteries and veins, and the display module is appropriate in size to be strapped around the abdomen of a neonate.

In diagnosing congenital heart defects in neonate and pediatric patients, there is often a need to sample the oxygen saturation in a variety of locations throughout the chambers of the heart and in the great vessels. This oxygen saturation data is normally collected in conjunction with an angiographic study of the heart, and it permits the operation of a malformed heart to be more accurately diagnosed, thereby resulting in more appropriate treatment for the patient. Currently, oxygen saturation data is collected by drawing multiple blood samples through a small catheter from a variety of locations throughout the heart and the great vessels. These blood samples are sequentially transferred to a blood gas analyzer to obtain an oxygen saturation reading for each sample. Using the technology of the present invention, a small oxygen sensor mounted on a probe or guidewire of suitable size such as less than 0.023" in diameter and 50 to 150 cm in length can be advanced through a guiding catheter to various locations in the heart and the great vessels to sample the oxygen saturation in vivo, thereby reducing the risk to the patient by eliminating the need to draw a large number of blood samples from a small subject and by reducing the time for the procedure.

In one aspect of the invention, an apparatus for use with a patient having a vessel carrying blood to ascertain characteristics of the blood is provided. The apparatus comprises a display module and a probe having a distal extremity adapted to be inserted into the vessel of the patient and having a proximal extremity coupled to the display module. The probe includes a gas sensor assembly mounted in the distal extremity for providing an electrical signal to the display module when the probe is disposed in the blood. The probe has an antithrombogenic surface treatment for inhibiting the adhesion of blood components to the probe when disposed in the blood.

In another aspect of the invention, a probe for use in a patient having a vessel carrying blood to ascertain characteristics of the blood is provided. The probe comprises a cannula adapted to be inserted into the vessel of the patient and a gas sensor assembly mounted inside the cannula. The cannula has an antithrombogenic surface treatment for inhibiting the adhesion of blood components to the cannula when disposed in the blood.

In a further aspect of the invention, a probe for use in a patient having a vessel carrying blood to ascertain characteristics of the blood is provided. The probe comprises a cannula having proximal and distal extremities, the distal extremity being adapted to be inserted into the vessel of the patient. A gas sensor assembly is mounted inside the distal extremity of the cannula. The cannula has an annular window of a gas permeable material extending around the gas sensor assembly.

Another aspect of the invention provides a probe for use in a patient having a vessel carrying blood to ascertain characteristics of the blood. The probe comprises a cannula having proximal and distal extremities, the distal extremity being adapted to be inserted into the vessel of the patient. An electrolyte solution is disposed in the cannula. A gas sensor assembly is mounted in the distal extremity of the cannula and includes an electrode disposed in the electrolyte solution. A conductor extends to the electrode and a sealing glass extends around the conductor. The conductor has a coefficient of thermal expansion and the sealing glass has a coefficient of thermal expansion approximating the coefficient of thermal expansion of the conductor for inhibiting separation of the conductor from the sealing glass and thus inhibiting the electrolyte solution from creeping between the conductor and the sealing glass.

A further aspect of the invention provides an apparatus for use with a patient having a vessel carrying blood to ascertain characteristics of the blood. The apparatus comprises a display module and a probe, the probe having proximal and distal extremities. The distal extremity of the probe is adapted to be inserted into the vessel of the patient and has a gas sensor assembly for providing an electrical signal when the probe is disposed in the blood. The display module has a first connector and the proximal extremity of the probe has a second connector for mating with the first connector. The second connector has a cylindrical portion and an electrical contact extending around at least a portion of the cylindrical portion. A conductor extends though the probe for electrically coupling the gas sensor assembly with the electrical contact. The electrical contact is seated flush with the cylindrical portion so as to provide the second connector with a substantially smooth cylindrical surface. The first and second connectors permit connection and disconnection between the probe and the display module.

In yet another aspect of the invention, a probe for use with an introducer in a patient having a vessel carrying blood to ascertain characteristics of the blood is provided. The probe comprises a cannula having proximal and distal extremities. The distal extremity of the cannula is adapted to be inserted into the vessel of the patient. A gas sensor assembly is disposed in the distal extremity of the cannula for providing an electrical signal when the cannula is disposed in the blood. A connector is provided on the proximal extremity of the cannula. The distal extremity of the cannula is adapted for slidable travel through the introducer when inserting the cannula into the vessel. The cannula and connector have a size which permits the introducer to be slid off of the proximal extremity of the cannula and the connector after the distal extremity of the cannula has been inserted into the vessel.

An aspect of the invention also provides an apparatus for use with a patient having a vessel carrying blood to ascertain characteristics of the blood. The apparatus comprises a compact display module and a probe, the probe having a proximal extremity coupled to the display module and a distal extremity adapted to be inserted into the vessel of the patient. The distal extremity includes a sensor for providing an electrical signal to the display module when the probe is disposed in the blood. The probe has calibration coefficients. The display module has a processor for processing the electrical signal to provide a reading and a memory for storing the calibration coefficients. The processor is coupled to the memory to permit access by the processor to the calibration coefficients in connection with the processing of the electrical signal so as to enhance the accuracy of the reading.

A kit for use with a patient having a vessel carrying blood to ascertain characteristics of the blood is provided in another aspect of the invention. The kit comprises a package. A probe is carried within the package. The probe has a distal extremity adapted to be inserted into the vessel of the patient and includes a sensor for providing an electrical signal. The probe has calibration coefficients. A compact display module is carried within the package and has a processor and a nonvolatile memory coupled to the processor. The calibration coefficients are stored in the memory of the display module. When the probe is coupled to the display module and the distal extremity inserted into the vessel and an electrical signal is received by the display module for providing a reading, the processor accesses the memory so as to utilize the calibration coefficients and thus enhance the accuracy of the reading.

A further aspect of the invention provides a probe for use in a patient having a vessel carrying blood to ascertain characteristics of the blood. The probe comprises a cannula adapted to be inserted into the vessel of the patient and having proximal and distal extremities. An electrolyte solution is disposed in the distal extremity of the cannula. A gas sensor assembly is mounted in the distal extremity of the cannula and is disposed in the electrolyte solution. The gas sensor assembly has a tube with a distal portion and a first electrode coiled around the tube. A second electrode is carried by the distal portion of the tube. First and second conductors extend from the proximal extremity of the cannula to the gas sensor assembly, the first conductor being coupled to the first electrode and the second conductor extending through the tube and being coupled to the second electrode. The tube serves as support for the first electrode and as a conduit for the second conductor.

A probe for use in a patient having a vessel carrying blood to ascertain characteristics of the blood is also provided. The probe comprises a cannula having proximal and distal extremities. The distal extremity is adapted to be inserted into the vessel of the patient. A flex circuit extends through at least a portion of the cannula. The flex circuit has proximal and distal portions with first and second electrodes formed on the distal portion and first and second conductors extending from the proximal portion to the first and second electrodes. An electrolyte solution is disposed in the distal extremity of the cannula in the vicinity of the first and second electrodes.

EXAMPLES OF THE INVENTION

Numerous probes and display modules according to the present invention have been fabricated and tested to demonstrate the feasibility and performance of the device. The following experimental data illustrates the typical performance of the invention under experimental conditions.

Figure 11:
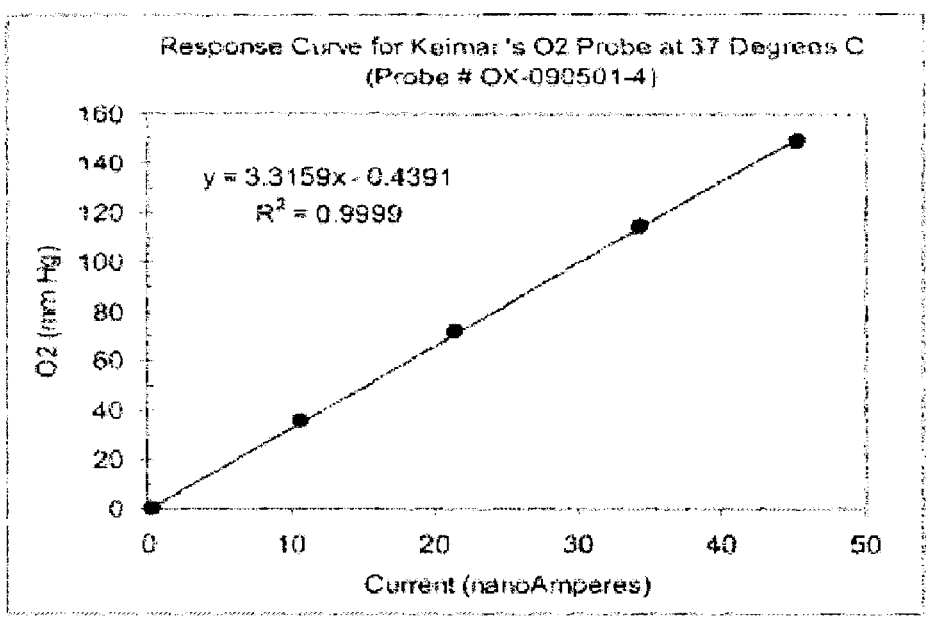
FIG. 11 is a chart illustrating performance of an example oxygen sensor probe.

Chart 1, illustrated in FIG. 11, shows the performance of a representative example of an oxygen sensor probe over a range of dissolved oxygen concentrations from zero to 150 mmHg partial pressure of oxygen. The response is linear over the range of interest, making the calibration to 5% accuracy a simple process.

Figure 12:
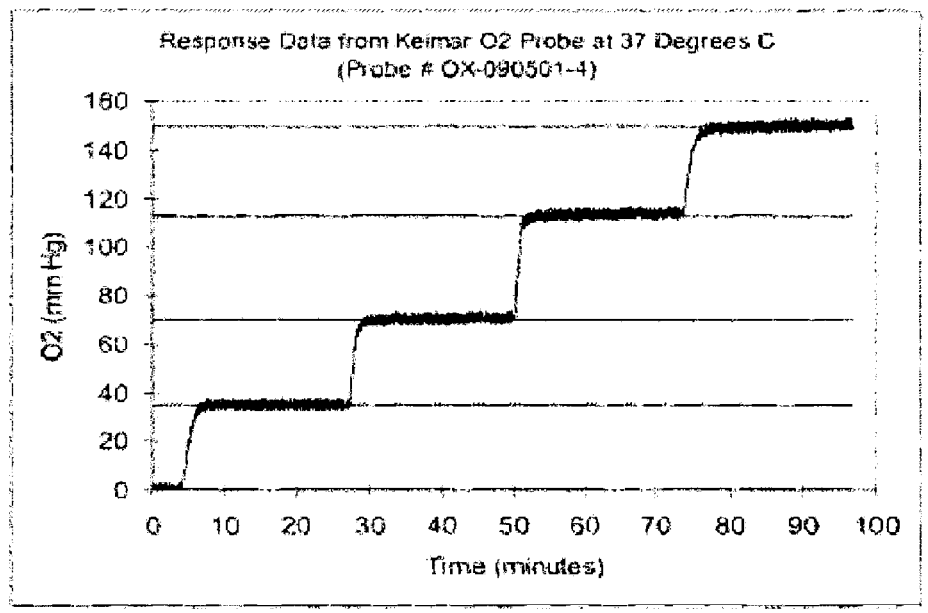
FIG. 12 is a chart illustrating time response of an example oxygen sensor probe.

Besides exhibiting accuracy and linearity, the oxygen sensor provides rapid response to changes in the dissolved oxygen concentration. Chart 2, illustrated in FIG. 12, shows the time response of a representative oxygen sensor probe to a sequence of step changes in oxygen partial pressure, demonstrating a settling time of less than 3 minutes to within 5% of the final value.

Figure 13:
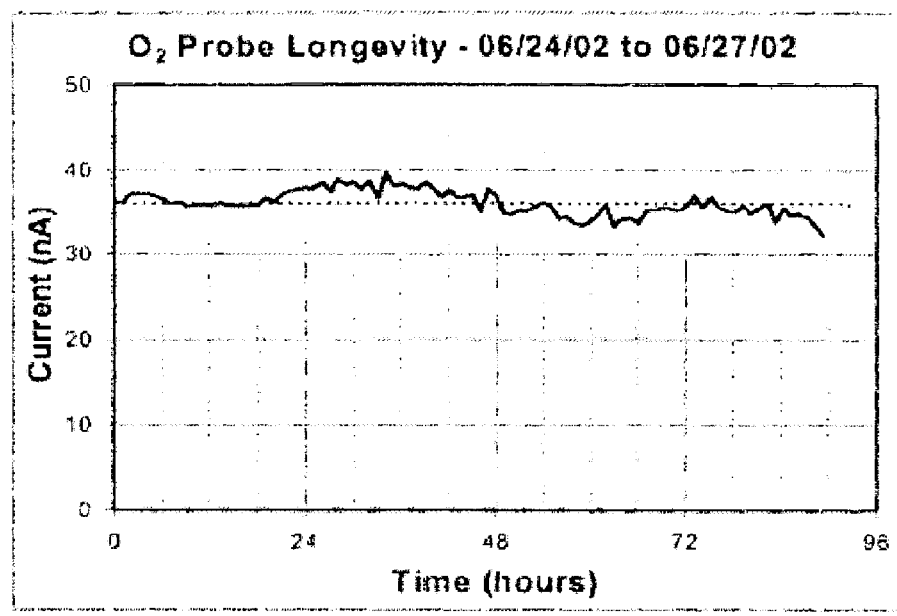
FIG. 13 is a chart illustrating stability of output of an example oxygen sensor.

Besides demonstrating accuracy, linearity, and rapid response, the oxygen sensor provides greater than 72 hours of longevity to satisfy the requirements of the ICU/CCU monitoring application. Chart 3, illustrated in FIG. 13, shows the stability of the oxygen sensor output over the course of a 90-hour longevity study. With a constant, room air, partial pressure of oxygen of 150 mmHg, the output of the sensor remains nearly constant for greater than 72 hours except for the expected small variations in output due to temperature fluctuations and noise.

Figure 14:
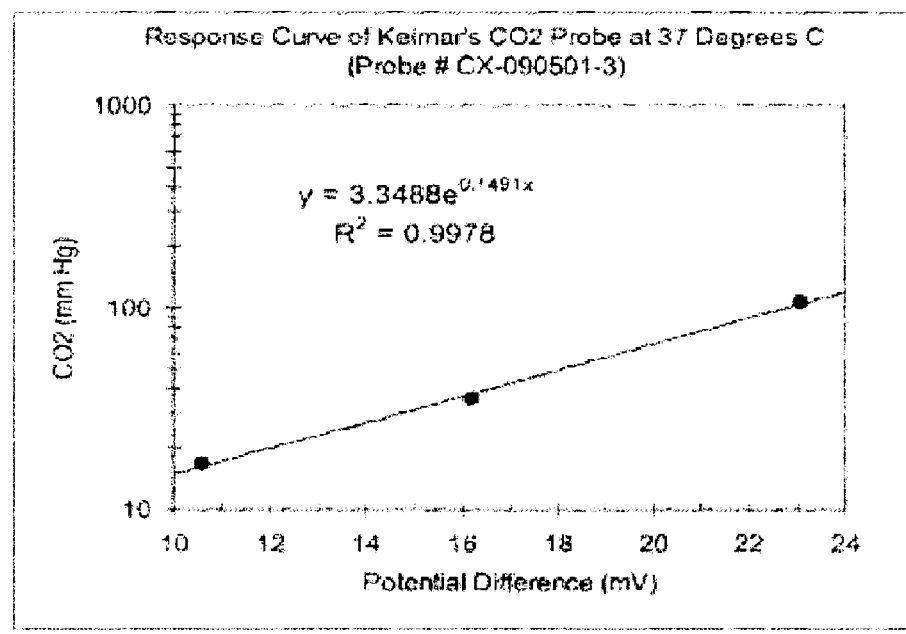
FIG. 14 is a chart illustrating performance of an example carbon dioxide sensor probe.

Chart 4, illustrated in FIG. 14, shows the performance of a representative example of a carbon dioxide sensor probe over a range of dissolved carbon dioxide concentrations from 10 to 100 mmHg partial pressure of carbon dioxide. The response shows the classic logarithmic performance expected for this type of pH-responsive sensor, making calibration to 5% accuracy a simple process.

Figure 15:
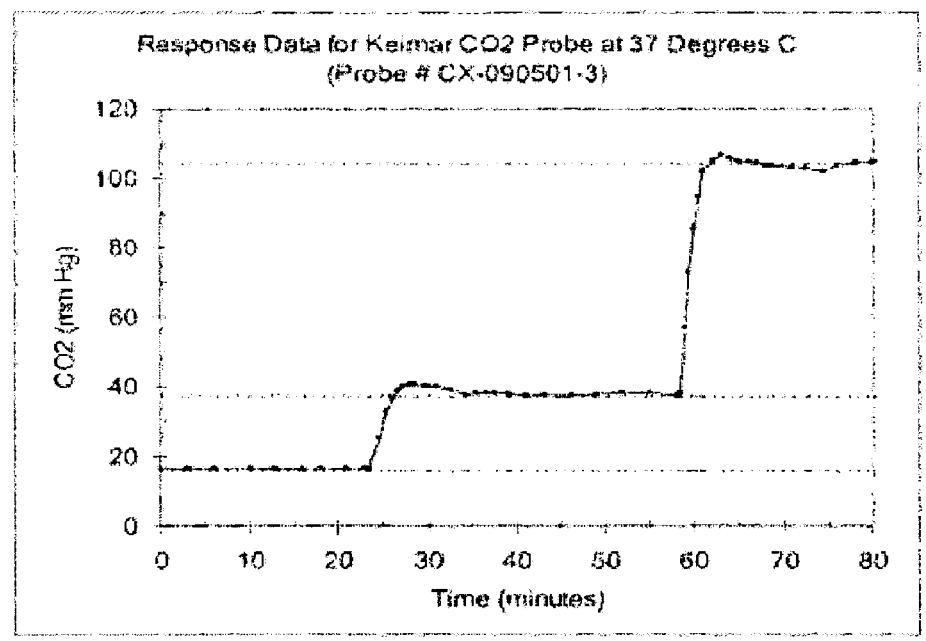
FIG. 15 is a chart illustrating time response of an example carbon dioxide sensor probe.

Besides exhibiting accuracy and linearity, the carbon dioxide sensor provides rapid response to changes in the dissolved carbon dioxide concentration. Chart 5, illustrated in FIG. 15, shows the time response of a representative carbon dioxide sensor probe to a sequence of step changes in carbon dioxide partial pressure, demonstrated a settling time of less than three minutes to within 5% of the final value.

Besides demonstrating accuracy, linearity, and rapid response, the carbon dioxide sensor has an inherently long lifetime, since it does not consume the electrodes or the electrolyte solution as the oxygen sensor does.

Figure 16:
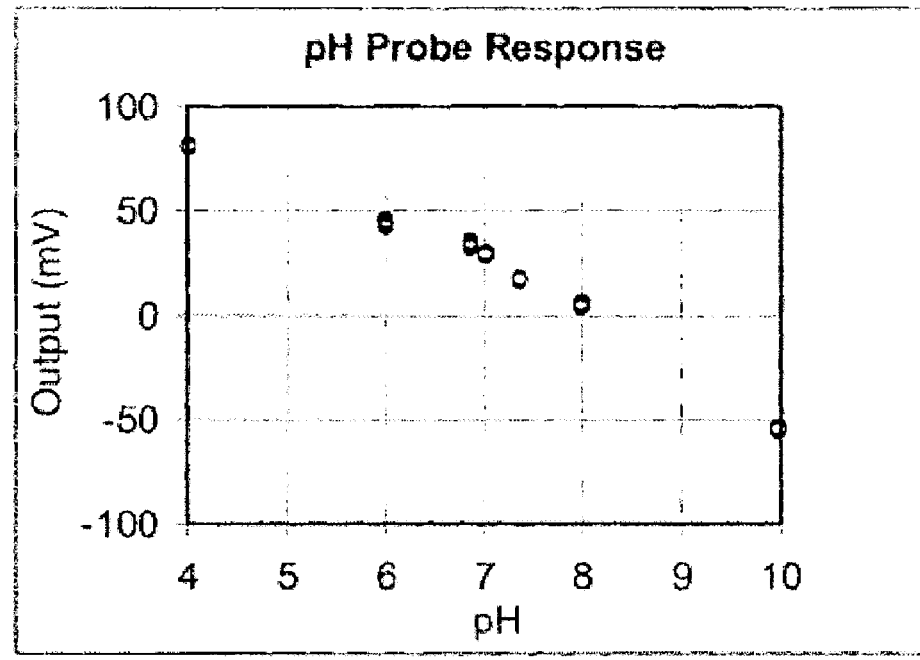
FIG. 16 is a chart illustrating performance of an example pH sensor probe.

Chart 6, illustrated in FIG. 16, shows the performance of a representative pH sensor output over a range of pH from 4 to 10. This pH sensor is mounted in a multi-sensor probe that also includes oxygen, carbon dioxide, and temperature sensors. The response shows the classic linear voltage response to the logarithmic pH parameter. The standard deviation for repeated measurements at a single pH value is approximately 0.02 pH, demonstrating that calibration to the required 0.05 pH accuracy over the physiological range of pH from 7 to 8 is feasible.

The response time of the pH sensor is fast, with a settling time of approximately 10 seconds to a step change in the pH value.

This sample data shows that the oxygen, carbon dioxide, and pH sensors according to the present invention provide the accuracy, response time, and longevity to meet the needs of the medical monitoring applications for which it is intended.

All of the sample probes have outside diameters of 0.020" as described in the preferred embodiment, and a single probe includes the four oxygen, carbon dioxide, temperature, and pH sensors. While the invention is susceptible to various modifications and alternative forms, specific examples thereof have been shown in the drawings and are herein described in detail. It should be understood, however, that the invention is not to be limited to the particular forms or methods disclosed, but rather the invention is to cover all modifications, equivalents and alternatives falling within the spirit and scope of the appended claims.

What is claimed is:

1. A probe for use with an introducer in a patient having a vessel carrying blood to ascertain characteristics of the blood comprising a cannula having proximal and distal extremities, the distal extremity of the cannula being adapted to be inserted into the vessel of the patient, an oxygen and carbon dioxide sensor assembly disposed in the distal extremity of the cannula for providing an electrical signal when the cannula is disposed in the blood, the cannula being made of a gas-permeable material in the vicinity of the oxygen and carbon dioxide sensor assembly, and a connector carried by the proximal extremity of the cannula whereby the distal extremity of the cannula is adapted for slidable travel through the introducer when inserting the cannula into the vessel, the cannula and connector having a size which permits the introducer to be slid off of the proximal extremity of the cannula and the connector after the distal extremity of the cannula has been inserted into the vessel and whereby the oxygen and carbon dioxide sensor assembly is mounted in the distal extremity of the cannula and comprises an electrically insulating conduit having a distal portion, a first working electrode, a second working electrode, a first reference electrode and a second reference electrode, first, second, third, and fourth conductors extending from the proximal extremity of the cannula to the oxygen and carbon dioxide sensor assembly, wherein the first conductor is electrically coupled to the first working electrode and the second conductor extends through the electrically insulating conduit and is coupled to the second working electrode, the third conductor is electrically coupled to the first reference electrode, and the fourth conductor is electrically coupled to the second reference electrode, the electrically insulating conduit serving as a support for the first reference electrode and as a conduit for the fourth conductor.

2. The probe of claim 1 further comprising a flex circuit extending through at least a portion of the cannula, the flex circuit having proximal and distal portions with first and second electrodes formed on the distal portion and first and second conductors extending from the proximal portion to the first and second electrodes, the first and second electrodes and the first and second conductors forming at least part of the oxygen and carbon dioxide sensor assembly.

3. The probe of claim 2 wherein at least part of the proximal portion of the flex circuit serves as the connector.

4. The probe of claim 2 wherein the flex circuit has an exposed surface, the first and second electrodes each being a pad formed on the exposed surface.

5. A small-diameter probe for use with an introducer in a patient having a vessel carrying blood to ascertain characteristics of the blood comprising a cannula having proximal and distal extremities, the distal extremity of the cannula being adapted to be inserted into the vessel of the patient, an oxygen and carbon dioxide sensor assembly disposed in the distal extremity of the cannula for providing an electrical signal when the cannula is disposed in the blood and a connector carried by the proximal extremity of the cannula whereby the distal extremity of the cannula is adapted for slidable travel through the introducer when inserting the cannula into the vessel, the cannula and connector having a size which permits the introducer to be slid off of the proximal extremity of the cannula and the connector after the distal extremity of the cannula has been inserted into the vessel and wherein the sensor assembly comprises at least one insulating layer surrounding a proximal working electrode of a proximal sensor and at least one insulating layer surrounding a distal working electrode of a distal sensor, the proximal sensor comprising a proximal reference electrode and the distal sensor comprises a distal reference electrode, wherein both of said reference electrodes extend at least partially around the at least one insulating layer and wherein the distal working electrode, or a conductor in electrical contact with and extending from the distal working electrode, extends through the at least one insulating layer surrounding the proximal working electrode, where at least one of the working electrodes encircles at least one insulating layer.

6. The probe of claim 1 where the insulating conduit is a tube.

7. The probe of claim 1 where the first working electrode extends at least partially around the insulating conduit.

8. The probe of claim 7 where the first reference electrode extends at least partially around the insulating conduit.

9. The probe of claim 1 where the second reference electrode extends at least partially around the electrically insulating conduit.

* * * * *

UNITED STATES PATENT AND TRADEMARK OFFICE
CERTIFICATE OF CORRECTION

PATENT NO. : 7,630,747 B2 Page 1 of 1
APPLICATION NO. : 10/658926
DATED : December 8, 2009
INVENTOR(S) : Corl et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1057 days.

Signed and Sealed this

Twenty-first Day of December, 2010

David J. Kappos
*Director of the United States Patent and Trademark Office*